United States Patent [19]
Paul

[11] Patent Number: 5,318,897
[45] Date of Patent: Jun. 7, 1994

[54] MONOCLONAL ANTIBODY AND ANTIBODY COMPONENTS ELICITED TO A POLYPEPTIDE ANTIGEN GROUND STATE

[75] Inventor: Sudhir Paul, Omaha, Nebr.

[73] Assignee: Igen, Inc., Rockville, Md.

[21] Appl. No.: 789,344

[22] Filed: Nov. 8, 1991

Related U.S. Application Data

[63] Continuation-in-part of Ser. No. 498,225, Mar. 23, 1990, Pat. No. 5,229,272, which is a continuation-in-part of Ser. No. 343,081, Apr. 25, 1989, Pat. No. 5,236,836.

[51] Int. Cl.$^5$ .................. C12P 21/06; C12N 9/00; C07K 15/28
[52] U.S. Cl. .................. 435/68.1; 435/188.5; 530/388.9
[58] Field of Search .............. 435/68.1, 188.5; 530/388.9

[56] References Cited

U.S. PATENT DOCUMENTS

| | | | |
|---|---|---|---|
| 4,196,265 | 4/1980 | Koprowski et al. | 435/7 |
| 4,376,110 | 3/1983 | David et al. | 436/513 |
| 4,492,751 | 1/1985 | Boguslaski et al. | 435/7 |
| 4,493,890 | 1/1985 | Morris | 435/7 |
| 4,659,567 | 4/1987 | Tramontano et al. | 424/85 |
| 4,792,446 | 12/1988 | Kim et al. | 424/85.8 |
| 4,888,281 | 12/1989 | Schochetman et al. | 435/72 |
| 4,900,674 | 2/1990 | Benkovic et al. | 435/232 |

FOREIGN PATENT DOCUMENTS

| | | |
|---|---|---|
| 125023 | 11/1984 | European Pat. Off. |
| WO86/06742 | 11/1986 | PCT Int'l Appl. |
| US89/01951 | 5/1989 | PCT Int'l Appl. |
| PCT/US89/-01950 | 11/1989 | PCT Int'l Appl. |
| WO90/05144 | 5/1990 | PCT Int'l Appl. |
| WO90/05746 | 5/1990 | PCT Int'l Appl. |

OTHER PUBLICATIONS

Paul, S. et al. (1992) J. Biol. Chem. 267 (19), 13142–13145.

"Abzylutely Spot On", The Economist, 80–81 (Feb. 7, 1987).

"Abzymes", Scientific American, 256, No. 2, 84–85 (1987).

Affinity Chromatography Principles and Methods, Pharmacia, pp. 12–18, Uppsala Sweden (1986).

Altschuh, D. et al., "Localization of Antigenic Determinants of a Viral Protein by Inhibition of Enzyme-Linked Immunosorbent Assay (ELISA) with Tryptic Peptides", J. Immunology Methods, v. 50, p. 99 (1982).

Amit, A. G. et al., "Three-Dimensional Structure of an Antigen-Antibody Complex at 2.8 A Resolution", Science 233: 747 (1986).

Amzel, L. M. et al., "Three-Dimensional Structure of Immunoglobulins", Ann. Rev. Biochem. 48:961 (1979).

Anglister, J. et al., "NMR study of the Complexes Between a Synthetic Peptide Derived from the B Subunit of Cholera Toxin and Three Monoclonal Antibodies Against It", Abstract, American Chemical Soc. (1988), 006–2960/88/0427–0717.

"Antibody Catalyzes Stereospecific Reaction", Science/Technology Concentrates, C&EN, 15 (Aug. 31, 1987).

Aruffo, A. et al., "Molecular Cloning of a CD38 cDNA by a high-efficiency COS cell expression system", Proc. Natl. Acad. Sci., 84:8573–8577 (1987).

Atassi, M. Z., "Surface-Simulation Synthesis and Its Application in Protein Molecular Recognition", Protein Engineering-Application in Science, Medical and Industry, pp. 125–153 Edited by Inouye, M. and Sarma, R., Academic Press (1986).

(List continued on next page.)

Primary Examiner—Charles L. Patterson, Jr.
Attorney, Agent, or Firm—Curtis, Morris & Safford

[57] ABSTRACT

What is disclosed is a catalytic monoclonal antibody able to cleave a polypeptide and in particular, a catalytic monoclonal antibody elicited by a ground state antigen is disclosed. Antigens include, among others, the polypeptide, a derivative of the polypeptide, a fragment of the polypeptide or any of these bound to a carrier molecule. Methods of making and using the catalytic monoclonal antibody are also disclosed.

16 Claims, 9 Drawing Sheets

OTHER PUBLICATIONS

Azuma, T. et al., "Diversity of the Variable-Joining Region Boudary of λ Light Chains has a Pronounced Effect on Immunoglobulin Ligand-Binding Activity", *Proc. Natl. Acad. Sci. USA*, v. 81, p. 6139, (Oct. 1984).

Baldwin E. and Schuyltz, P. G., *Generation of a catalytic antibody by site-directed mutagenesis. Science*, 245, 1104–1107 (1989).

Barrett, A. J., *Proteinase Inhibitors* (Editors A. J. Barrett and G. Salvesen), pp. 3–22, Elsevier, London, (1986).

Baum, R., "Catalytic Antibody Cuts Peptide Bond", *C & E N*, 5, 7–8 (1989).

Baum, R., "Catalytic Antibodies Open Up New Strategy For Protein Engineering", Science, *C&EN*, 30–33 (April 6.

Benjamini, E. et al., "Immunochemical Studies on the Tobacco Mosaic Virus Protein. VI Characterization of Antibody Population Following Immunization with TMV Protein", *Biochemistry*, v.7, No. 4, pp. 1253–1260 (1968).

Benjamini, E. et al., "Immunochemical Studies on the Tobacco Mosaic Virus Protein. VII. The Binding of Octanoylated Peptides of the TMV Protein with Antibodies to the Whole Protein", *Biochemistry*, v.7, No. 4, pp. 1261–1264 (1968).

Berchtold et al., *Blood*, vol. 74, No. 7, pp. 2414–2417 (1989).

Better, M. et al., "*Escherichia Coli* Secretion of an Active Chimeric Antibody Fragment", *Science*, 240: 1041–1043 (1988).

Blackburn, G. M. et al., "Catalytic Antibodies", *Biochem. J.* 262: 381 (1989).

Bloom, S. R. et al., "Autoimunity in Diabetics Induced by Hormonal Contaminants of Insulin", *Lancet* i:14–17 (1979).

Brown, G. and Ling, N. R., Murine Monoclonal Antibodies. In *Antibodies: A Practical Approach* (Ed"D. Cathy) IRL Press, Oxford, U.K. vol. 1, pp. 81–104 (1988).

Bulletin Office Of Public Information, Berkeley Campus, University of California (Dec. 9, 1986).

Burd, J. et al., "Specific Protein-Binding Reactions Monitored by Enzymatic Hydrolysis of Ligands--Fluorescent Dye Conjugates", *Analytical Biochemistry*, 77, 56–67 (1977).

"Cancer Breakthrough Seen-IGEN Discovers New Protein Class", *Rockville Gazette* (Jan. 21, 1987).

Chalufour, A. et al., "Rare Sequence Motifs are Common Constituents of Hypervariable Antibody Regions", *Ann. Inst. Pasteur/Immunology*, 138:671, Elsevier, Paris (1987).

Chaudhary, V. J. et al., "A recombinant immunotoxin consisting of two antibody variable domains fused to *Pseudomonas* exotoxin", *Nature* 339: 394 (1989).

Chothia, C. et al., "Canonical Structures for the Hypervariable Regions of Immuonoglobulins", *J. Mol. Biol.* 196: 901 (1987).

Chothia, C. et al., "The Predicted Structure of Immunoglobulin D1.3 and Its Comparison with the Crystal Structure", *Reports*, 755 (Aug. 1986).

Cochran, A. G. et al., "Photosensitized Cleavage of a Thymine Dimer by an Antibody", *J. Am. Chem. Soc.*, 110: 7888–7890 (1988).

Colman, P. M. et al., "Three-Dimensional Structure of a Complex of Antibody with Influenza Virus Neuraminidase", *Nature* 326: 358 (Mar. 1987).

Corey, D. R. et al., "Generation of a Hybrid Sequence-Specific Single-Stranded Deoxyribonuclease", *Reports* 1401 (Dec. 1987).

Creighton, T. E. Disulfide bonds between cystein residues. In Protein Structure: A Practical Approach (Ed. T. E. Creighton) IRL Press, Oxford, U.K., pp. 155–167.

David, G. S. et al., "The Hybridoma-An Immunochemical Laser", *Clin, Chem., 27 (9), 1580–1585 (1981)*.

Davies, D. R., Padlan, E. A. and Sheriff, S.: Antibody-antigen complexes. *Ann. Rev. Biochem.*, 59, 439–474 (1990).

de la Paz, P. et al., "Modelling of the Combining Sites of Three-Anti-Lysozyme Monoclonal Antibodies and of the Complex Between One of the Antibodies and its Epitope", *EMBO J.*, 5:2, 415 (1986).

Dimaline, R. et al., "A novel VIP from elasmobranch intestine has full affinity for mammalian pancreatic VIP receptors", *Biochimica et Biophysica Acta*, 930, 97–100 (1987).

Dimaline, R. et al., "Purification and Characterization of VIP from Two Species of Dogfish", *Peptides*, 7 (Suppl. 1): 21–26 (1986).

Dixon, M. et al., *Enzymes*, Third Edition, London, (1979).

Durfor, C. N. et al., "Antibody Catalysis in Reverse Micelles", *J. Am. Chem. Soc.* 110, 8713 (1988).

OTHER PUBLICATIONS

Edelman, G. M. et al., "Reconstitution of Immunologic Activity by Interaction of Polypeptide Chains of Antibodies", *Proc. Natl. Acad. Sci.*, 50: 753–761 (1963).

Emr, S. D. et al., "Sequence analysis of mutations that prevent export of λ receptor, an *Escherichia coli* outer membrane protein", *Nature*, 285: 82–85 (1980).

Erhan, S. et al., "Do immunoglobulins have proteolytic activity?", *Nature*, v.251, pp. 353–355 (Sep. 27, 1974).

Fisher, G., "Acyl Group Transfer-Aspartic Proteinases", *Enzyme Mechanisms* (Editors: M. I. Page and A. Williams), Royal Society of Chemistry, London, 230 (1987).

*FPLC TM Ion Exchange and Chromatofocusing–Principles and Methods*, Pharmacia, pp. 59–106, Uppsala, Sweden (1987).

Frackelton, Jr., A. R., et al., "Functional Diversity of Antibodies Elicted by Bacterial β-D Galactosidase", *J. Bio. Chem.*, 255 (11), 5286–5290 (1980).

Franek, F. and Wezlin, R. S., *Biokhimiya*, 28: 193 (1963).

Franek, F. and Nezlin, R. S., "Recovery of Antibody Combining Activity By Interaction of Different Peptide Chains Isolated from Purified Horse Antitoxins", *Folia Microbiol.*, 8: 128–130 (1963).

French, D. L., R. Laskow, and M. D. Scharff. The role of somatic hypermutation in the generation of antibody diversity. *Science* 244, 1152 (1989).

Gavish, M. et al., "Preparation of a Semisynthetic Antibody", Abstract, *Am. Chem. Soc.* (1978), 006-2960/78/0417-1345.

Geysen, H. M. et al., "*A Priori* Delineation of a Peptide Which Mimics a Discontinous Antigenic Determinant", *Molecular Immunology*, 23:7 p. 709 (1986).

Giam, C. Z. et al., "*In Vivo* and *In Vitro* Autoprocessing of Human Immunodeficiency Virus Protease Expressed in *Escherichia Coli*", *J. Biol. Chem.*, 263: 14617–14620 (1985).

Gish et al., *J. Med Chem.*, 14: 1159–1162, (1971).

Hansen, D., "Antibodies with Some Bite", *Nature*, 325, 304 1987).

Harper, J. W. et al., "Enzymatically Active Angiogenin/Ribonunclease A Hybrids Formed by Peptide Interchange", Abstract, *Am. Chem. Soc.* (1988), 006-2960/88/0427-0219.

Hendershot, L. M. et al., "Identity of the Immunogolobulin Heavy-Chain-Binding Protein with the 78,000–Dalton Glucose-Regulated Protein and the Role of Posttranslational Modifications in Its Binding Function", *Mol. and Cellular Bio.*, 8(10), 4250–4256, (1988).

Highfeld, R., "Aids Drug A Step Nearer", *The Daily Telegraph*, 9, (Aug. 4, 1987).

Hilvert, D. et al., "Catalysis of Concerted Reactions by Antibodies: The Claisen Rearrangement", *Proc. Natl. Acad. Sci. USA*, v. 85, pp. 4953–4955 (Jul. 1988).

Hochman, J. et al., "An Activity Antibody Fragment (Fv) Composed of the Variable Portions of Heavy and Light Chains", *Biochemistry* 12: 1130 (1973).

Huse, W. D. et al., "Generation of a Large Combinatorial Library of the Immunoglobulin Repertoire in Phage, Lambda", *Science*, 246: 1275–1281 (1989).

Inbar, D. et al., "Localization of Antibody-Combining Sites within the Variable Portions of Heavy and Light Chains", *Proc. Natl. Acad. Sci. USA*, 69: 2659 (1972).

Inbar, D. et al., "Crystallization with Hapten of the Fab Fragment from a Mouse IgA Myeloma Protein with Antidinitrophenyl Activity", *J. of Biol. Chem.* 246: 6272 (1971).

Itoh, N. et al., "Human Preprovasoactive Intestinal Polypeptide Contains A Novel PHI-27 -Like Peptide, PHM-27", *Nature* 304: 547–549 (1983).

Iverson, B. L. et al., "Sequence-Specific Peptide Cleavage Catalyzed by an Antibody", *Science* 243:1184 (1989).

Jackson, D. Y. et al., "An Antibody-Catalyzed Claisen Rearragement", *J. Am. Chem. Soc.* 110, 4841 (1988).

Jackson, D. Y. et al, *Proc. Nat'l. Acad. Sci.* 88(1) 58–67 (1991).

Jacobs, J. et al., "Catalytic Antibodies", *J. Am. Chem. Sco.*, 109, 2174–2176 (1987).

Janda, K. D. et al., "Induction of an Antibody that Catalyzes the Hydrolysis of an Amide Bond", *Science* 241, 1188–1191 (1988).

Jaton, J. C. et al., "Recovery of Antibody Activity Upon Reoxidation of Completely Reduced Polyalanyl Heavy Chains and Its Fd Fragment Derived from Anti--2,4–dinitrophenyl Antibody", *Biochemistry*, 7: 4185–4195 (1968).

Jencks, W. P., "Catalysis in Chemistry and Ezymology", 282–320, 288 (McGraw Hill, New York) (1969).

OTHER PUBLICATIONS

Jencks, W. P., "What Everyone Wanted to Know About Tight Binding and Enzyme Catalysis, but Never Thought of Asking", *Molecular Biol. Biochem. & Biophys.*, 32, 3–25, (1980).

Jencks, W. P., "Binding Energy, Specificity and Enzymic Catalysis: The Circe Effect", *Adv. Enzym.*, 43, 219–410 (1975).

Jerne, N. K. et al., "Recurrent Idiotopes and Internal Images", *EMBO J.*, v. 1, No. 2, 243–247 (1982).

Jue et al., Biochemistry 17, 5399–5406, (1978).

Kabat, E. A. et al., "Sequences of Proteins of Immunological Interest (5th Edition)", V. 1, 2, 3, U.S. Department of Health and Human Services (1991).

Klein, J. Immunology, John Wiley & Sons, N.Y., (1982) pp. 162–164.

Knisley, K. A. et al., "Affinity Immunoblotting. High Resolution Isoelectric Focusing Analysis of Antibody Clonotype Distribution", *J. Immunological Methods*, 95, 79–87, Elsevier (1986).

Koerner and Nieman, "High Performance Liquid Chromatographic Determination of Glucosides", *J. Chromatography* 449, 216–228, (1988).

Kohen, F. et al., "Monoclonal Immunoglobulin G Augments Hydrolysis of an Ester of the Homologous Hapten", *FEBS Letters*, 111, 427–431 (1980).

Kohen, F. et al., "Antibody-Enhanced Hydrolysis of Steroid Esters", *Biochimica et Biophysica Acta*, 629, 328–337 (1980).

Kohen, F. et al., "A Steroid Immunoassay Based on Antibody-Enhanced Hydrolysis of a Steroid-Umbelliferone Conjugate", *FEBS Letters*, 110, 137–140 (1979).

Kohen, F. et al., "Nonradioisotopic Homogeneous Steroid Immunoassays", *J. Steroid Biochemistry*, 11, 161–167 (1979).

Kohler, G. et al., "Continous Cultures of Fused Cells Secreting Antibody of Predefined Specificity", *Nature* 256: 445–497 (1975).

Kozbor, D. et al., "The Production of Monoclonal Antibodies from Human Lymphocytes", *Immunology Today* 4:72–79, (1983).

Kozbor, D. et al., "Establishment of Anti-TNP Antibody-Producing Human Lymphoid Lines by Preselection for Hapten Binding Followed by EBV Transformation", *Scand. J. Immunol.*, 10:187–194, (1979).

Kubiak, T. et al., "Synthetic Peptides $V_H$(27–68) and $V_H$(16–68) of the Myelona Immunoglobulin M603 Heavy Chain and their Association with the Natural Light Chain to Form an Antigen Binding Site", Abstract, *Am. Chem. Soc.* (1987), 006-2960/87/0426-7849.

Kwan, S. et al., "Production of Monoclonal Antibodies", *Genetic Engineering*, 2, 31–46, (1980).

Larrick, J. W., Danielsson, L., Brenner, C. A., Abrahamson, M., Fry, K. E. and Borrebaeck, C. A. K.: Rapid cloning of rearranged immunoglobulin genes from human hybridoma cells using mixed primers and the polymerase chain reaction. *Biochem. Biophys. Res. Commun.*, 160, 1250–1256, (1989).

Lee, F. et al., "Isolation and Characterization of a mouse interleukin cDNA clone that expresses B-cell stimulatory factor 1 activities and T-cell and mast-cell stimulating activities", *Proc. Natl. Acad. Sci. U.S.A.* 83: 2061–2065 (1986).

Lerner, R. A. et al., "Catalytic Antibodies", *Scientific American*, 258(3), 42–50 (1988).

Lerner, R. A. et al., "Antibodies as Enzymes", *Trends Biochem. Science*, 12(11), 427–430 (1987).

Lerner, R. A. et al., "At the Crossroads of Chemistry and Immunology: Catalytic Antibodies", *Science*, 252, 659–667 (May 1991).

Lerner, R. A., "Antibodies of Predetermined Specificity in Biology and Medicine", *Adv. In Immun.*, 36, 1–40 (1984).

Loh, E. Y. et al., "Polymerase Chain Reaction with Single-Sided Specificity: Analysis of T Cell Receptor & Chain", *Science*, 243: 217–220 (1989).

Lorberboum-Galski, H. et al., "Cytotoxic Activity of an Interleukin 2-*Pseudomonas* Exotoxin Chimeric Protein Produced in *Escherichia coli*", *Proc. Natl. Acad. Sci. U.S.A.*, 85: 1922–1926 (1988).

MacDonald, R. J. et al., "Isolation of RNA Using Guanidinium Salts", *Meth. Enzymol.*, 152: 219–226 (1987).

Machleidt, W. et al., "Mechanism of Inhibition of Papain by Chicken Egg White Cystatin", (Biomedical Division, Elsevier Science Publishers), v. 243, No. 2, p. 234, (Jan. 1989) 00145793/89.

"Making Antibodies Act Like Enzymes", *Science News*, 130, Nos. 25 & 26 (Dec. 20 & 27, 1986).

Mariuzza, R. A. et al., "The Structure Basis of Antigen–Antibody Recognition", *Ann. Rev. Biophys. Chem.*, 16: 139 (1987).

Marx, J., "Making Antibodies Work Like Enzymes", *Science* 234, 1497–1498 (1986).

OTHER PUBLICATIONS

Massey, R., "Catalytic Antibodies Catching On", *Nature*, 328, No. 6129, 457–458 (1987).

Meek, T. D. et al., "Inhibition of HIV-1 Protease in Infected T-Lymphocytes by Synthetic Analogues", *Nature*, 343: 390–392 (1990).

Mei, S., Mody, B., Eklund, S. H. and Paul S.: VIP hydrolysis by antibody Light chains. *J. Biol. Chem.* 266, 15571-15574.

Melchers, F. et al., "Enhanced Stability Against Heat Denaturization of E. Coli Wild Type and Mutant β-Galactosidase in the Presence of Specific Antibodies", *Biochemical and Biophysical Research Communications*, 40(3), 570–575 (1970).

Meldal, M. et al., Breddam, K., *Analytical Biochemistry*, 195, 141-147, (1991).

Mierendorf, R. C. et al., "Direct Sequencing of Denatured Plasmid DNA", *Meth. Enzymol.*, 152: 556-562 (1987).

Milstein, C., "Monoclonal Antibodies", *Scientific American*, 243(4), 66–74 (1980).

Moe, K., "Scripps, UC Create 'Killer' Antibodies", *S. D. Union*, (Dec. 12, 1986).

Mutt, V. Vasoactive Intestinal Peptide and related peptides: Isolation and chemistry. *Annals of the New York Academy of Sciences* 527, 1-19 (1988).

Mutter, M., "The Construction of New Proteins and Enzymes-A Prospect for the Future?", *Agnew. Chem. Int. Ed. Engl.* 24, p. 639 (1985).

Napper, A. "A Stereospecific Cyclization Catalyzed by an Antibody", *Science*, 237, 1041-1043 (1987).

Nilsson, A., "Structure of the Vasoactive Intestinal peptide from Chicken Intestine. The Amino Acid Sequence", *FEBS Letters*, 60: 322-326 (1975).

Nishi, N. et al., "Apparent Autolysis of the N-Terminal Tetrapeptide of VIP", *Chem. Pharm. Bull.* 31(3), p. 1067 (1983).

Nobeyuki et al., *Nature*, vol. 304, pp. 547–549 (1983).

Offord, R. E., "Review Protein Engineering by Chemical Means?", *Protein Engineering*, v. 1, No. 5, p. 151 (1987).

Opstad, K., "The Plasma VIP Response to Exercise is Increased After Prolonged Strain, Sleep and Energy Deficiency and Extinguished by Glucose Infusion", *Peptides*, 8, 175-178 (1986).

Orlandi, R. et al., "Cloning Immunoglobul in variable domains for expression by the polymerase chain reaction", *Proc. Natl. Acad. Sci. U.S.A.*, 86: 3833-3837 (1989).

Paul, S. et al., "Elevated Levels of Atrial Natriuretic Peptide and Vasoactive Intestinal Peptide in Exercising Man", Abstract, *Clin. Res.*, 35: 112A (1987).

Paul, S. et al., "Characterization of Receptors for Vasoactive Intestinal Peptide from the Lung", *J. Biol. Chem.* 262: 158-162 (1987).

Paul, S. et al., "Autoantibody to Vasoactive Intestinal Peptide in Human Circulation", *Biochem. Biophys. Res. Commun.* 130: 479-485 (1985).

Paul et al. *J. of Biol. Chem.* 266, 16128-16134 (1991).

Paul, S. et al., "Regulatory Aspects of the VIP Receptor in Lung", *Annals of New York Academy of Science*, v. 527, pp. 282-295 (Jun. 1988).

Paul, S. et al., "Human Autoantibody to Vasoactive Intestinal Peptide: Increased Incidence in Muscular Exercise", *Life Sciences* 43: 1079-1084 ((1988).

Paul, S. et al., "Affinity Chromatography of Catalytic Autoantibody to Vasoactive Intestinal Peptide", *J. Immunology*, v. 145, No. 4, pp. 1196-1199 (Aug. 1990).

Paul, S. et al., "High Affinity Peptide Histidine Isoleucine-Preferring Receptors in Rat Liver", *Life Sciences*, v. 41, pp. 2373-2380 (1987).

Paul S. et al., "Purification of [$^{125}$I]-Vasoactive Intestinal Peptide by Reverse-Phase HPLC", *Peptides* 5: 1085-1087 (1987).

Paul, S. et al., "Autoabzyme Catalyzed Cleavage of Vasoactive Intestinal Peptide", *Progress in Immunology*, v. VIII, pp. 833-836 (editors F. Melchers et al.) Springer Verlag, Berlin (1989).

Paul, S., Volle, D. J., Powell, M. J. and Massey, R. J.: Site specifically of a catalytic vasoactive intestinal peptide antibody: An inhibitory VIP subsequence distant from the scissile peptide bond. *J. Biol. Chem.*, 265, 11910-11913 (1990).

Paul, S., Johnson, D. J. and Massey, R. J. Binding epitopes and multiple hydrolytic sites recognized by catalytic antibodies. in *CIBA Foundation Symp. 159 on Catalytic Antibodies*, in Press, (1991).

Paul, S., "A New Effector Mechanism for Antibodies: Catalytic Cleavage of Peptide Bonds", *Cold Spring Harbor Symposium on Immunological Research*, v. 54 (1989).

OTHER PUBLICATIONS

Paul. S., Mei, S., Mody, B., Eklund, S. H., Beach, C. M., Massey, R. J. and Hamel, F. Cleavage of VIP at multiple sites by autoantibodies. *J. Biol. Chem.* 266, 16128–16134 (1991).

Paul, S. et al., "Catalytic Hydrolysis of Vasoactive Intestinal Peptide by Human Autoantibody", *Science*, 244: 1158–1162 (1989).

Paul, S.: A new effector mechanism for antibodies: Catalytic cleavage of peptide bonds. *Cold Spring Harb. Symp. Quant. Biol.*, 54, 283–286 (1989).

Paul, S. et al., "Characterization of Autoantibodies to VIP in Asthma", *J. Neuroimmunology*, 23: 133–142 (1989).

Pauling, L., "Nature of Forces Between Large Molecules of Biological Interest" *Nature*, 161: 707 (1948).

*PhastGel Silver Kit Instruction Manual*, Pharmacia, Uppsala, Sweden (1987).

Pollack, S. J. et al., "Selective Chemical Catalysis by an Antibody", *Science*, 234, 1570–1573 (1986).

Pollack, S. J. et al., "Antibody Catalysis by Transition State Stabilization", *Cold Spring Harbor Symposium on Quantitative Biology*, 52, 97–104 (1987).

Porter, R. R. et al., "Subunits of Immunoglobulins and their relationship to Antibody Specificity", *J. Cell Physiol.*, 67 (Suppl. 1): 51–64 (1966).

Raso, V. et al., "The Antibody–Enzyme Analogy. Comparison of Enzymes and Antibodies Specific for Phosphopyriodoxyltyrosine", *Biochemistry*, 14, 591–599 (1975).

Raso, V. et al., "Antibodies Specific for Conformationaly Distinct Coenzyme Substrate Transition State Analogs.", *J. Am. Chem. Soc.*, 95(5), 1621–1628 (1973).

Raso, V. et al., "The Antibody–Enzyme Analogy. Characterization of Antibodies to Phosphopyridoxyltyrosine Derivatives", *Biochemistry*, 14, 584–591 (1975).

Rees, A. R. et al., "Investigating Antibody Specificity Using Computer Graphics And Protein Engineering", *Trends in Biochemical Sciences*, 11: 144 (Mar. 1986).

Rich, D. H., "Inhibitors of Aspartic Proteinases", *Proteinase Inhibitors* (Editors A. J. Barrett and G. Salvesen), Elsevier, pp. 179–217 (1986).

Roberts, R. J., "Directory of Restriction Endonuclease", *Methods In Enzymology*, 68, 27–31 (Academic Press, New York, R. Wu, Editor) (1979).

Roberts, S. et al., "The Cloning and Expression of an Anti-peptide Antibody: A System for Rapid Analysis of the Binding Properties of Engineered Antibodies", (IRL Press Limited, Oxford, England) p. 59.

Roder, J. et al., "The EBV-Hybridoma Technique", *Methods In Enzymology*, 121: 140–167 (1986).

Roholt, O. et al., "Specific Combination of H and L Chains of Rabbit γ-Globulins", *Proc. Natl. Acad. Sci.*, 51: 173–178 (1964).

Rosselin, G., "The receptors for the VIP Family Peptides (VIP, Secretin, GRF, PHI, PHM, GIP, Glucagon and Oxyntomodulin). Specificities and Indentity.", *Peptides*, 7(Suppl. 1): 89–100 (1986).

Royer, G. P., "Enzyme-Like Synthetic Catalysts (Synzymes)", *Advances In Catalysis*, 29: 197–227 (1980).

Ruff, M. R. et al., "CD4 Receptor Binding Peptides that Block HIV Infectivity cause Human Monocyte Chemotaxis", *FEBS Letters*, 211: 17–22 (1987).

Sacerdote, P. et al., "Vasoactive Intestinal Peptide 1-12: A Ligand for the CD4 (T4)/Human Immunodeficiency Virus Receptor", *J. of Neuroscience Res.*, 18: 102–107 (1987).

Sacks, D. L. et al., "Immunization of Mice Against African Trypanosomiasis Using Anti-Idiotypic Antibodies", *J. Expr. Med.*, 155, 1108–1119 (1982).

Sastry, L., et al., "Cloning of the immunological repertoire in *Escherichia coli* for generation of monoclonal catalytic antibodies", *Proc. Natl. Acad. Sci. U.S.A.*, 86: 5728–5732 (1989).

Schultz, P. G., "Catalytic Antibodies", *Acc. Chem. Res.*, 22: 287 (1989).

Schultz, P. G., "The Interplay Between Chemistry and Biology in the Design of Enzymatic Catalysts", *Science*, 240: 426 (1988).

Tramontano, A. et al., "Catalytic Antibodies", *Science* 234: 1566–1570 (1986).

Tramontano, A. et al., "Specificity and Mechanism of Esterolytic Antibodies", *J. of Cellular Biochemistry*, Supp. 11C, Abstract W 417, p. 238 (1987).

Tramontano, A. et al., "Chemical Reactivity at an Antibody Binding Site Elicited by Mechanistic Design of a Synthetic Antigen", *Proc. Natl. Acad. Sci. U.S.A.*, 83: 6736–6740 (1986).

Tramontano, A. et al., "Antibody Catalysis Approaching the Activity of Enzymes", *J. Am. Chem. Soc.* 110: 2282 (1988).

Turner, J. T. et al., "Characterization of the VIP Receptor in Rat Submandibular Bland: Radioligand Binding Assay in Membrane Preparations", *J. Pharmacol. Exp. Therap.* 242: 873–881 (1987).

OTHER PUBLICATIONS

Unkeless, J. C. et al., "Structure and Function of Human and Murine Receptors for IgG", *Ann. Rev. Immunology*, 6: 251-281 (1988).

Van der Eb, A. J. et al., "Assay of Transforming Activity of Tumor Virus DNA", *Meth. Enzymol.*, 65: 826-839 (1980).

Van Brunt, J., "Antibodies Find a New Role-As Enzymes", *Biotechnology*, 5: 767 (1987).

Van Regenmortel, R. H. V., *Synthetic Peptides as Antigens*, Laboratory Techniques in Biochemistry and Molecular Biology Series (Editors R. H. Burdon and P. H. van Knippenberg), 19: 1-39 (1988).

Ward, E. S. et al., "Binding activities of a repertoire of single immunoglobulin variable domains secreted from *Escherichia coli*", *Nature*, 341: 544-546 (1989).

White, A. et al., *Principles of Biochemisty*, 200, 201, 217-221, 573, 575 and 585 (McGraw Hill Book Company, New York, Fourth Edition) (1968).

Winter, G. P., "Antibody Engineering", *Phil Trans. R. Soc. Lond.*, B 324, 537-547 (1989).

Woie, L. et al., "Increase in Plasma VIP in Muscular Exercise", *Gen. Pharmacol.*, 17:321-326 (1987).

Wong, G. C. et al., "Human GM-CSF: Molecular Cloning of the Complementary DNA and Purification of the Natural and Recombinant Proteins", *Science*, 288: 810-815 (1985).

Yang, Y. C. et al., "Human IL-3 (Multi-CSF): Identification by Expression Cloning of a Novel Hematopoietic Growth Factor Related to Murine IL-3", *Cell*, 47: 3-10 (1986).

Yokota, T. et al., "Isolation and characterization of a human interleukin cDNA clone, homologous to mouse B-cell stimulatory factor 1, that expresses B-cell and T-cell stimulatory activities", *Proc. Natl. Acad. Sci. U.S.A.*, 83: 5894-5896 (1986).

Hiller, Susanne, "A Better Way to Make the Medicine Go Down", *Science*, 253, 1095-1096 (1991).

Shenkin, P. S. et al., "Predicting Antibody Hypervariable Loop Conformation. I. Ensembles of Random Conformations for Ringlike Structures", *Biopolymers* 26: 2053 (1987).

Sheriff, S. et al., "Three-Dimensional Structure of an Antibody-Antigen Complex", *Proc. Natl. Acad. Sci. U.S.A.*, 84: 8075 (1987).

Shokat, K. et al., "An Antibody-Mediated Redox Reaction", *Agnew. Chem. Int. Ed. Engl.* 27: 1172 (1988).

Shokat, K. M. et al., "A New Strategy for the Generation of Catalytic Antibodies", *Nature*, v. 338, pp. 269-271 (Mar. 1989).

Skerra, A. et al., "Assembly of a Functional Immunoglobulin $F_v$ Fragment in *Escherichia coli*", *Science*, 240: 1038-1043 (1988).

Slobin, L., "Preparation and Some Properties of Antibodies with Specificity Towards p-Nitrophenylesters", *Biochemistry*, 5: 2836-2844 (1966).

Smith-Gill, S. J. et al., "Contributions of Immunoglobulin Heavy and Light Chains to Antibody Specificity for Lysozyme and Two Haptens", *J. Immunology*, 139: 4135 (1987).

Steinitz, M. et al., "EB Virus-Induced B Lymphocyte Cell Lines Producing Specific Antibody", *Nature* 269: 420-422 (1977).

Steinitz, M. et al., "Establishment of a Human Lymphoblastoid Cell Line with Specific Antibody Production Against Group A Streptococcal Carbohydrate", *Immunobiology*, 156: 41-47 (1979).

Steinitz, M. et al., "Continuous Production of Monoclonal Rheumatoid Factor by EBV-Transformed Lymphocytes", *Nature*, 287: 443-445, (1980).

Stewart, J. M. et al., "Solid Phase Peptide Synthesis", Pierce Chemical Co., Rockford, Ill. (1984).

Suckling, C. J., Tedford, C. M., Proctor, G. R., Khalaf, A. I., Bence, L. M. and Stimson, W. H. *1991 Catalytic Antibodies*, Wiley, Chichester (Ciba Foundation Symposium 159) pp. 201-210.

Summers, Jr., J. B., "Catalytic Principles of Enzyme Chemistry: Antibody Models and Stereo Electronic Control", Harvard University Ph.D. Thesis, 22-101 (1983).

Sun, L. K. et al., *Proc. Natl. Acad. Sci. U.S.A*, 84: 214-218 (1987).

Tramontano, A. et al., "Antibodies as Enzymic Catalysts", *J. Cellular Biochemistry*, Supp. 11C, p. 199, Abstract N 022 (1987).

MONOCLONAL ANTIBODY AND ANTIBODY COMPONENTS ELICITED TO A POLYPEPTIDE ANTIGEN GROUND STATE

This application is a continuation-in-part of copending application U.S. patent application Ser. No. 07/498,225, filed Mar. 23, 1990, now U.S. Pat. No. 5,229,272, which is a continuation-in-part of 07/343,081, filed Apr. 25, 1989, now U.S. Pat. No. 5,236,836.

FIELD OF THE INVENTION

This invention relates to antibodies able to enhance the rate of chemical reaction of reactants and in particular of peptides and polypeptides. More particularly it relates to monoclonal antibodies elicited to a polypeptide antigen and methods of making and using these antibodies.

Several publications are referenced in this application by Arabic numerals within parentheses in order to more fully describe the state of the art to which this invention pertains as well as to more fully describe the invention itself. Full citations for these references are found at the end of the specification immediately preceding the claims.

BACKGROUND OF THE INVENTION

The forces involved in ligand binding by antibodies and substrate binding by enzymes is similar, viz., hydrogen bonding, electrostatic interaction and hydrophobic effect. The energy obtained from enzyme-substrate binding may be visualized to force electronic strain in the substrate and facilitate the formation of a transition state. There is strong evidence for the theory that enzymes bind the transition state of the reaction they catalyze better than the ground state, resulting in a reduced free energy of activation for the reaction (1). The transition state theory is based upon the observation that the reactants for a chemical reaction normally exist at a ground state energy level. In order for a reaction to proceed, the energy level of the reactants must be raised to that required to form transition state intermediate(s). A successful catalyst may function to reduce the energy requirement for the formation of such transition state intermediate compound(s). This has come to be known as the transition state theory of enzymatic catalysis.

Other factors that may facilitate enzymatic catalysis include the proximity and orientation effects-apposition of correctly oriented reactants within the active site of the enzyme would reduce the requirement for a large number of random collisions prior to a productive reactant interaction. In principle, antibodies could catalyze chemical reactions by similar means.

The first report of chemical conversion of a ligand by an antibody appeared in 1980 (2), but the steroid ester hydrolysis by a rabbit polyclonal antiserum described in this report was stoichiometric rather than catalytic.

Massey et al, U.S. Pat. No. 4,888,281 were the first to report catalyzing a chemical reaction by means of an antibody elicited to a reactant, a reactant bound to a peptide or other carrier molecule, a reaction intermediate or analogs of the reactant, product or a reaction intermediate.

Subsequently, antibodies have been demonstrated to catalyze or facilitate chemical reactions, including acyl transfer (3-6), pericyclic (7-8) and redox reactions (9).

It is generally believed that reported antibodies (3-9) obtain their catalytic properties, like enzymes, from their ability to bind the transition state of the reactant better than its ground state.

Various analogs of the transition state of reactants have been used as antigens in the elicitation of immune responses (10).

The requirement for a hapten which antigenically mimics the transition state complicates efforts to obtain desirable catalytic antibodies. It would be advantageous if catalytic antibodies could be elicited to a ground state, as an antigen. Suckling et al. (11) have reported the use of a ground state antigen comprising a hapten related in structure to the substrate to elicit an antibody able to catalyze a Dieis-Alder reaction (the addition of acetoxybutadiene to N-substituted maleimides) and an antibody able to cleave beta lactam rings). Cleavage of peptide bonds by means of antibodies elicited to a selected peptide-metal complex has been demonstrated with the assistance of metal cofactors by Iverson et al. (12). Iverson et al. utilized a Co(III)triethylenetetramine (trien)-peptide hapten in order to elicit an antibody able to accept a metal complex with chemical reactivity into the binding pocket.

The discovery, isolation and characterization of naturally occurring autoantibodies, i.e., antibodies produced by an animal's immune system to the animal's own cellular component (self-antigen), as opposed to an antigen introduced by immunization, which enhance the rate of a chemical reaction, is disclosed in copending U.S. patent application Ser. No. 343,081, filed Apr. 4, 1989. These autoantibodies have been shown to enhance the rate of cleavage of one or more peptide bonds in vasoactive intestinal peptide (VIP). The natural occurrence of these catalytic autoantibodies in multiple humans suggests that there is a common, naturally occurring antigen capable of eliciting these autoantibodies. Classical catalytic antibody theory suggests that the naturally occurring autoantibody must be formed in response to a high energy transition state intermediate or in response to an unusually charged analog of the peptide. It would therefore not be expected that the antigen is the ground state of a peptide, or is a large precursor protein that is eventually digested to yield the peptide, for example, pro-VIP.

It is also known that antibody binding is energetically most favored by the presence of the entire H-chain and L-chain binding site (13). The $V_H$ fragments of anti-lysozyme antibodies bind the antigen with an affinity of only 10% of the intact antibody (14). L-chains are also likely to participate in antigen binding interactions, although most studies suggest that the contribution of L-chains is smaller than that of H-chains (15-17). It would not be expected that an antibody component smaller than an intact catalytic antibody would possess the favorable steric conformation provided by the intact catalytic antibody to permit the catalysis of a peptide bond without the assistance of a metal trien cofactor as taught by Iverson et al.

Improved antibodies and methods for selectively eliciting antibodies able to catalyze a chemical reaction of a peptide of interest are of singular interest for therapeutic products and other purposes.

The use of a ground state antigen would eliminate the necessity for preparing stable analogues of transition state intermediates or haptens complexed with metal co-factors so that catalytic antibodies specific for a polypeptide of interest may be elicited as needed.

There are obvious advantages that single chain proteins offer over multichain proteins (antibodies), both from the point of view of structure-function analysis as well as pharmacological and therapeutic stability. It would be advantageous if the binding and catalytic domains on an antibody were either the same or closely positioned to one another such that the benefits of catalytic activity could be achieved by a simple protein as opposed to a multichain antibody. Heretofore, the art has not demonstrated the capability of using such components of an antibody for catalytic purposes. Similar advantages are offered by dimers formed of the several combinations of light and heavy chains. Nor has the art demonstrated that an antibody light chain elicited by a ground state reactant will have catalytic activity.

OBJECTS OF THE INVENTION

It is thus a primary object of this invention to provide catalytic antibodies and catalytic antibody fragments for reactions of interest using ground state antigens rather than transition state analogs to elicit an immune response.

It is a further and related object of this invention to provide catalytic antibodies and catalytic antibody fragments for polypeptide reactions of interest using ground state antigen to elicit an immune response.

It is still a further object of this invention to provide catalytic antibodies and catalytic antibody fragments for the hydrolytic cleavages of polypeptides of interest.

It is still a further specific object of this invention to provide antibody catalyst and antibody fragment catalysts for the cleavage of specific polypeptides, e.g. vasointestinal peptide.

SUMMARY OF THE INVENTION

These and other objects of the invention are achieved by catalytic antibodies elicited by a ground state polypeptide antigen. In one embodiment the invention is directed to a method for catalyzing a chemical reaction of a polypeptide by a catalytic antibody wherein the catalytic antibody is elicited by an antigen comprising the polypeptide, a derivative of the polypeptide or a fragment of the polypeptide. In yet another embodiment the invention is directed to a method for catalyzing a chemical reaction of a reactant by a catalytic antibody light chain wherein the catalytic antibody light chain is derived from an antibody elicited by an antigen comprising the reactant, a derivative of the reactant or a fragment of the reactant.

BRIEF DESCRIPTION OF THE DRAWINGS

The invention will be understood more clearly and fully understood from the following detailed description, when read with references to the accompany figures, in which.

DETAILED DESCRIPTION OF THE INVENTION

Definitions

Figure 1:
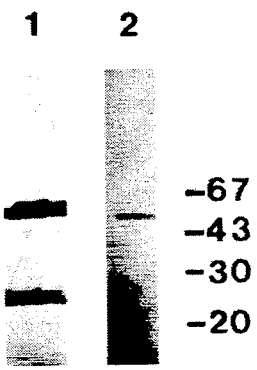
FIG. 1 shows silver stained SDS polyacrylamide gels showing monoclonal c23.5 IgG electrophoresed under reducing conditions (lane 1) and Fab electrophoresed under non-reducing conditions.

The term "chemical reaction" refers to a reaction wherein at least one reactant is converted to at least one product. The chemical reaction of a polypeptide may proceed by a number of different pathways, such as, for example, hydrolysis of one or more peptide bonds.

The term "animal" as used herein refers to any organism with an immune system and includes mammalian and non-mammalian animals.

Antibodies in accordance with the invention are elicited by presenting an antigen to immune cells. The antigen may be a protein, a polypeptide or a fragment or derivative of a protein or polypeptide either alone or coupled to a carrier.

In one embodiment, the chemical reaction is the cleavage of a peptide bond. Peptide bond as used herein refers to an amide bond linking two adjacent amino acid residues and is generically represented by the following formula wherein the peptide bond is shown within the box:

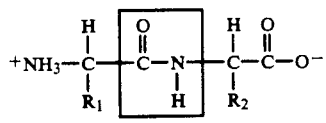

An amino acid consists of a carbon atom to which is bonded an amino group, a carboxyl group, a hydrogen atom and a distinctive group referred to as a "side chain" ($R_1$ and $R_2$ in the formula above). Amino acid as used herein includes the twenty naturally occurring amino acids which comprise the building blocks of proteins. It is understood by those skilled in the art that when either of the adjacent amino acids is proline, the respective side chains R$_1$ or R$_2$ are bonded to the adjacent nitrogen atoms to form the characteristic 5-membered proline ring.

The substrate can be any proteinaceous molecule such as, for example, a regulatory protein or a structural protein, and includes, but is not limited to, peptide hormones (e.g., insulin, growth hormone, secretin, etc.), peptide neurotransmitters and neuromodulators (e.g., vasoactive intestinal peptide, endorphins, enkephlins, bradykinins, substance P etc.) tumor proteins (e.g., oncogene products, carcinoembryonic antigens, etc.), bacterial proteins and vital proteins (e.g., human immunodeficiency viral(HIV) gp 120, influenza glycoproteins, etc.).

Rate enhancing antibodies may in general provide rate enhancement by either catalytic or stoichiometric mechanisms. The antibodies in accordance with the invention catalytically enhance the rate of the reaction and are therefore described as "catalytic antibodies".

A catalytic antibody in accordance with the invention is a substance which is capable of changing the rate of a chemical reaction, all other conditions (e.g., temperature, reactant/substrate concentration, etc.) being the same and which does not enter into the chemical reaction and therefore is not consumed in the reaction. It is also a substance which exhibits the capability of converting multiple moles of reactant/substrate per mole of catalytic antibody. From a mechanistic viewpoint the antibody binds the reactant/substrate, effects the accelerated conversion of the reactant/substrate to the product and then releases the product; and which changes the rate of the chemical reaction without shifting the position of the equilibrium. The aforementioned definitions are characteristics of ideal catalysts. However, in practice, even the best of catalysts become poisoned or deactivated by contamination in the reaction system or as a result of chemical or physical destruction during the reaction process. For reasons well known in the art, the true operation of a catalyst may be obscured by components of the reaction system or by the condition of the reaction environment.

The art has adopted certain working definitions to express catalytic activity. These expressions are [1]k$_{cat}$, or "turnover" and [2] k$_{cat}$/k$_{uncat}$, the "rate enhancement factor". Turnover indicates the number of molecules of reactant/substrate which can be converted to product per mole of catalytic antibody per unit time. For example, if a molecule exhibits a turnover of 10$^3$ molecules of substrate per minute and the molecule maintains its catalytic activity for 24 hours at room temperature and at its optimal pH, each molecule of catalyst would then make a total of 1.4×10$^6$ conversions, indicating its catalytic behavior. This total conversion is to be distinguished from the total conversion in a stoichiometric reaction, which will never exceed 1.0, no matter how long the reaction is carried out. The rate enhancement factor is a dimensionless number which expresses the rate of reaction in the presence of catalyst to the rate of reaction in the absence of catalyst, all other reaction conditions (e.g., reactant concentration, temperature, etc.) being equal.

Antibody and immunoglobulin refer to any of several classes of structurally related proteins that function as part of the immune response of an animal, which proteins include IgG, IgD, IgE, IgA, and IgM and related proteins. Antibodies are found in plasma and other body fluids and in the membrane of certain cells. Under normal physiological conditions (e.g. absent immunological dysfunction or human intervention) antibodies are produced by B cells (or the functional equivalent) of an animal in reaction to the entry of proteins or other chemical substances which that animal is not immunologically tolerant of into the tissue or body fluids of that animal.

Antibody and immunoglobulin as used herein refer to any component part of an antibody. These component parts may be any fragment or other portion of a classical antibody molecule (IgG, IgA, IgE, IgD, IgM and related classes and subclasses) which retains the desired antibody function and with which the invention may be practiced. The catalytic domain is the minimum peptide sequence which retains the catalytic property inherent in that amino acid sequence. Catalytic antibodies as used herein thus include any fragment or domain in which a binding region is involved in the catalysis.

Embodiments of the Invention

The invention provides an antibody able to catalyze a chemical reaction of a polypeptide, methods for eliciting an antibody able to catalyze a chemical reaction of a polypeptide, and methods of using the antibody to cause a selected polypeptide to undergo a chemical reaction. The antibody is elicited to a ground state antigen which, depending on the immunogenicity of the antigen, is a selected peptide, peptide derivative or peptide fragment, or is formed by coupling a selected peptide, peptide derivative or peptide fragment to any useful immunological carrier known to the art.

The invention also provides an antibody light chain able to catalyze a chemical reaction of a reactant including polypeptides and other substrates, methods for eliciting an antibody from which that light chain able to catalyze a chemical reaction may be derived, and methods for using the antibody to cause a selected reactant to undergo a chemical reaction. The antibody is elicited to a ground state antigen formed by coupling a selected reactant, reactant derivative or reactant fragment to any useful immunological carrier known to the art. The antibody thus elicited is then caused to separate into its component heavy and light chains, and the light chains are then isolated.

The antibodies of the invention can be monoclonal or polyclonal. Monoclonal antibodies are prepared by isolating lymphocytes from animals identified as having antibodies to a particular antigen, producing a plurality of hybridomas from the isolated lymphocytes and then screening the monoclonal antibodies produced by the hybridomas to identify monoclonal antibodies which enhance the rate of chemical reaction of the substrate. The antibody-producing lymphocytes are hybridized with myeloma cells, such as, for example SP2/0 or NS1 cells, to produce hybridoma cells. These hybridoma cells are then plated in the wells of microtiter plates. The monoclonal antibodies produced by the hybridoma cells are screened under appropriate conditions to identify monoclonal antibodies which enhance the rate of the reaction under appropriate conditions. The identification is made by treating a standardized solution of the reactant/substrate with an aliquot withdrawn from a microtiter well and screening for the presence of the desired product, as described above. By comparison with standardized samples of the desired product or reactant/substrate, rates of reaction can be quantified. In this manner, wells containing hybridoma cells producing catalytic monoclonal antibodies can be identified. The selected hybridoma cells were then cultured to yield colonies.

These colonies are further propagated in in vitro or in vivo systems. In the latter case, mice such as syngeneic BALB/C mice are inoculated intraperitoneally with the selected hybridoma cells and produce tumors, generally within two or three weeks. These tumors were accompanied by the production of ascites fluid which contains the desired monoclonal antibodies. The monoclonal antibodies are then separately recovered from the ascites fluid by conventional methods such as ultrafiltration, ultracentrifugation, dialysis and immunoaffinity chromatography.

Peripheral blood lymphocytes of an animal identified as having catalytic antibodies for a particular substrate can be stimulated to grow in culture and, therefore, can be immortalized using methodologies well known in the art. For example, the lymphocytes can be so stimulated using a virus, a chemical agent or a nucleic acid (e.g., an oncogene). A particularly advantageous virus for immortalization is Epstein Barr virus (EBV). Thus, catalytic antibodies can be produced by the transformed cells. The so transformed cells can then be cloned using known methods to provide a reliable source of large amounts of monoclonal antibodies having catalytic activity for a given substrate.

One skilled in the art will appreciate that the genes, or fragments thereof, coding for the variable region of the antibody can be expressed in prokaryotic and eukaryotic cells using recombinant DNA methodologies well known in the art.

In accordance with an embodiment of the invention, the separately recovered antibodies are contacted with a molecule (e.g., a substrate, antigen, etc.) under suitable conditions permitting the formation of a complex between the antibody and the molecule in order to achieve catalysis of a chemical reaction of the molecule. The skilled artisan will appreciate that the conditions suitable for complex formation can vary depending on the particular molecule and antibody under consideration. Accordingly, the methods of this invention may be practiced under a variety of reaction conditions, in vivo and in vitro, as long as the antibodies are not prevented from complexing with the molecules or otherwise rendered inactive. More specifically, suitable conditions for complex formation encompass solution phase and emulsion reaction systems including a variety of solvents and solvent systems, maintained at a pH value between about 6.0 and about 9.0, preferably between about 6.0 and about 8.5 and at a temperature from about 4° C. to about 50° C., preferably from about 20° C. to about 45° C. One of ordinary skill in the art will realize that the choice of solvent will depend on the type of reaction. For example, aqueous solvents are desirable for peptide bond cleavage while non-aqueous solvents can be used to achieve peptide bond formation. The ionic strength, $=\frac{1}{2} \Sigma\, c_i z_i 2$, where c is the concentration and z is the electronic charge of an ionic solute, should be maintained at a value below about 2.0 (ionic strength units), preferably between 0.1 and 1.5. The methods of the invention can be carried out at reduced or elevated pressure, but advantageously are practiced at ambient pressure. In addition to solution phase and emulsion reaction systems, suitable conditions also include the use of solid support materials to which the antibody is attached. Such solid support materials are well-known to those of ordinary skill in the art as are methods for attaching antibodies to them.

A specific embodiment of the invention is directed to an antibody to vasoactive intestinal peptide (VIP). VIP is a 28 amino acid peptide originally isolated from the intestine but now recognized to be a neuropeptide widely distributed in the central and peripheral nervous systems. There is evidence that VIP is a neurotransmitter in its own right. In addition, VIP may modulate neurotransmission by classical transmitters and has been implicated in regulation of blood pressure, bronchial tone, neuroendocrine activity and exocrine secretion. VIP appears to be the major neurobronchodilator in humans and a diminished influence of VIP on the airways may permit a dominance of constrictor influences, and may underlie airway hyperactivity in asthma.

VIP belongs to a family of structurally related peptides, other prominent members of which are peptide histidine isolucine (PHI), growth hormone releasing factor (GRF) and secretin. Like the peptides themselves, there is evidence that the receptors for VIP, GRF, PHI and secretin are related. Receptors for VIP are found in lung, vascular smooth muscle, brain, pancreas, skin, intestine and other tissues. The amino acids sequence (Seq ID No: 11) of VIP is as follows:

H S D A V F T D N Y T R L R K Q M A V K K
W L N S I L N—CO—NH$_2$

Monoclonal antibodies to VIP were prepared by methods well known to the art (19-25). In one embodiment of this invention, a series of mice were immunized by an antigen comprising vasoactive intestinal peptide (VIP) coupled to keyhole limpet hemocyanin (KLH). The sera of the mice was screened for the saturable ($Y^{10}$-$^{125}$I)VIP binding titer, and splenocytes from the mouse showing the greatest saturable ($Y^{10}$-$^{125}$I)VIP binding titer were used to prepare hybridomas. Hybridoma clones were grown as ascites in host mice and the resulting antibodies were purified from the ascites fluid. Antibodies c23.5 and c23.4 were purified and screened for VIP hydrolytic activity. Both antibodies hydrolyzed ($Y^{10}$-$^{125}$I)VIP, whereas irrelevant antibodies used as controls did not. An Fab fragment of c23.5 also demonstrated VIP hydrolytic activity.

While VIP is the exemplified substrate and hapten, it will be understood that any peptide may be used as a substrate and hapten.

It is well known that VIP is a natural polypeptide composed of the same amino acids found in other peptides and proteins. Several naturally occurring neurotransmitters and hormones are closely related in primary structure to VIP. These include: secretin, glucagon, growth hormone releasing factor, and helodermin (26). While VIP is the exemplified substrate and hapten, it will be understood that any peptide may be used as a substrate and hapten.

Many different bonds in VIP can be cleaved by the VIP autoantibodies disclosed in patent application U.S. Ser. No. 343,081, filed Apr. 4, 1989. (see also, Paul, S., et al. (27). Thus antibody-mediated cleavage is not restricted to a unique peptide bond. The scissile peptide bonds in VIP (e.g., Gln-Met, Ala-Val, Met-Ala, Lys-Lys) (Paul et al. supra) are also present in other polypeptides.

The catalytic antibodies cleave not only full-length VIP, but also a fragment of VIP [VIP(15-28)] (23). This shows that the N-terminal region of rIP is not required for antibody catalytic activity. This is important because the possibility has previously been considered that the N-terminal residues of VIP may facilitate autocleavage of this peptide (28).

Since the recognition of VIP by antibodies occurs by the same pattern as for other polypeptide antigens, viz., by recognition of linear or conformational epitopes composed of discrete peptide subsequences found in the parent antigen (29), it is likely that antibodies recognizing other polypeptide antigens will display catalytic activity, provided the conditions described below are met. The recognition sequence is a more important determinant than the type of bond to be cleaved. This conclusion is supported by studies showing that VIP(-22-28) inhibits cleavage of VIP at residues 16-17 by antibodies (23). Therefore, there is nothing unique about the VIP cleavage point.

Antibodies possess hypervariable antigen binding sites (30). The hypervariability is brought about by V-D-J junctional rearrangement and somatic hypermutation, and $10^{12}$ different antibodies can be synthesized by B-lymphocytes. Antibody molecules already fulfill the first criterion required of a catalyst, i.e., the ability to bind substrate. Catalysis by enzymes is brought about by positioning of specific amino acid residues (e.g., His, Set, Asp, Cys) or cofactors (e.g., metals) in the substrate binding site (31). Enzymes which cleave polypeptides, i.e. proteases, are inhibited by diisopropyl fluorophosphate (DFP), which blocks the residues having protease activity. Given that a large number of antibody binding sites are created by the immune system by natural mutagenesis, it is most probable that some antibodies directed against polypeptide antigens would contain protease activity in their binding sites. The presence of the protease activity in the binding site can be independent of the type of antigen. The only requirements that must be met are specific binding and presence of suitably positioned catalytic amino acids in the antibody active site.

Therefore, the skilled artisan will appreciate that the following description of anti-VIP catalytic antibodies and catalytic antibody light chains is by way of example only, and is not intended to limit the scope of the invention.

EXAMPLE 1

Murine Monoclonal Catalytic Antibodies

Conjugates of VIP and keyhole limpet hemocyanin (VIP-KLH) were prepared via coupling to primary $NH_2$ groups on VIP and to -SH groups on thiolated KLH using the crosslinking reagent gammamaleimidobutyryloxysuccinimide (GMBS). KLH (17 mg) was thiolated with iminothiolane (33) the thiolated KHL was fractionated on a gel filtration column (Biorad Econo-Pak 10 DG) and conjugated with 3 mg synthetic VIP that had previously been treated for 2 h with GMBS. The molar stoichiometry of the VIP:KLH conjunction was 360, estimated on the basis of depletion of thiol groups reactive with Ellman's reagent. Five mice were immunized with the resulting VIP-KLH. Primary immunization (in Freunds complete adjuvant) followed by two booster immunizations (in incomplete Freunds adjuvant) was at 2-week intervals using 10-50 µg VIP equivalents of the antigen conjugate, administered intraperitoneally. The final injection was an intrasplenic one (17 µg VIP equivalents). Splenocytes from the mouse with the greatest saturable $(Y^{10\text{-}125}I)VIP$ binding titer (10% binding, 1:200 serum dilution; assayed according to Paul et al. (34) were fused with NS-1 myeloma cells by the PEG method (35). Cells from three culture wells (c23.1, c23.4 and c23.5) positive for VIP binding antibody were cloned twice by limiting dilution and then grown as ascites in pristane-treated mice. Antibodies c23.5 and c23.4 (both identified to be $IgG_{2a}$, kappa by ELISA) were purified from tissue culture fluid or ascites fluid by ammonium sulfate precipitation and Protein G-Sepharose chromatography as described by Paul et al. (36). Both antibodies hydrolyzed $(Y^{10\text{-}125}I)VIP$ and the hydrolysis products were assayed by separation of intact and degraded peptides by trichloroacetic acid (TCA) precipitation. See Paul et al. (36) for the assay method. The detection of hydrolytic activity was a function of the concentration of the antibody. Surprisingly, no hydrolytic activity was observed at high antibody concentrations (>10 nM). The properties of one of the antibodies (c23.5) were analyzed further. The strategies utilized to characterize the monoclonal antibodies were similar to those used for human antibodies (19-25).

The hydrolytic activity of this antibody was confirmed by reverse phase HPLC of the reaction mixture. Treatment of $(Y^{10\text{-}125}I)VIP$ with this antibody resulted in the appearance of two early eluting peaks of radioactivity, corresponding to VIP fragments (retention times 46 and 50 min. compared to 66 min. of intact $(Y^{10\text{-}125}I)$-VIP.

Other monoclonal antibodies to VIP [c23.1 ($IgG_1$, kappa) and c.5162 ($IgG_1$, kappa); obtained from Dr. J. Porter, University of Texas Health Science Center, Dallas)] were shown to be without VIP hydrolytic activity. Irrelevant monoclonal antibodies purified from hybridoma tissue culture fluids (directed against insulin-degrading enzyme, LH-receptors, CD8 or whole T-lymphocytes; obtained from Monoclonal Antibody Core Facility, University of Nebraska) were examined for $(Y^{10\text{-}125}I)VIP$ cleaving activity, and were observed to be without such activity as were irrelevant antibodies purified from commercially available ascites fluid (Sigma Chemical Company, St. Louis, Mo.).

Figure 2:
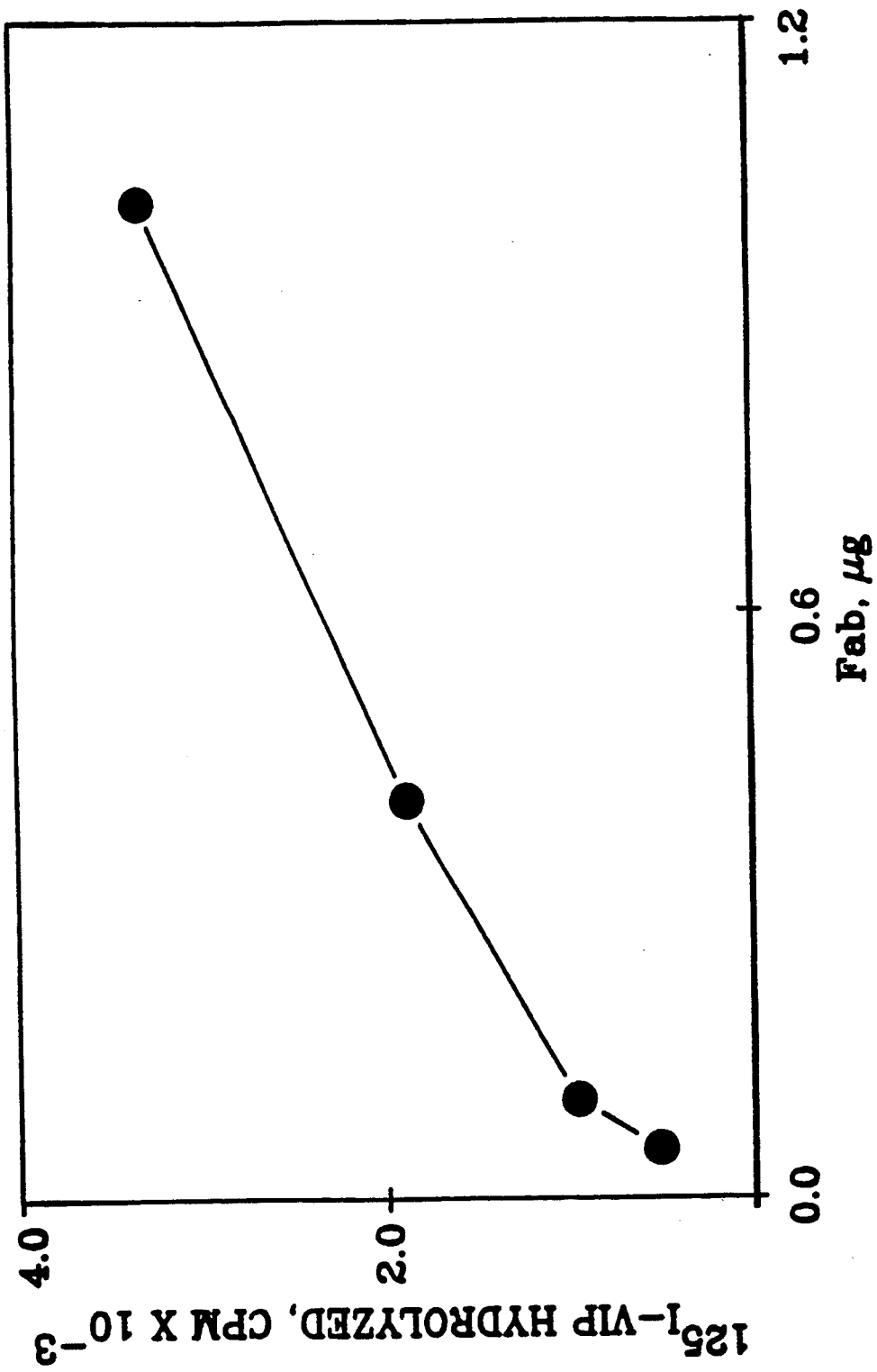
FIG. 2 shows the hydrolysis of $(Tyr^{20}-^{125}I)VIP$ by increasing concentrations of c23.5 Fab estimated as the amount of TCA-soluble radioactivity.

Fab was prepared by digestion of protein G-purified IgG with immobilized papain (Pierce; 16 mg protein per ml gel in 20 mM sodium phosphate, 10 mM EDTA. ph 7 for 2 h) and chromatography on an anion-exchange column (Mono Q; Pharmacia, Piscataway, N.J.); 0-1 NaCl in 20 mM Tris-HCl, pH 8, in 45 min). Fab, recovered in the unbound fraction, displayed a mass of 50 kD estimated by SDS-polyacrylamide gel electrophoresis (FIG. 1). With increasing Fab concentration, progressively increasing hydrolysis of VIP was observed (FIG. 2).

Figure 3:
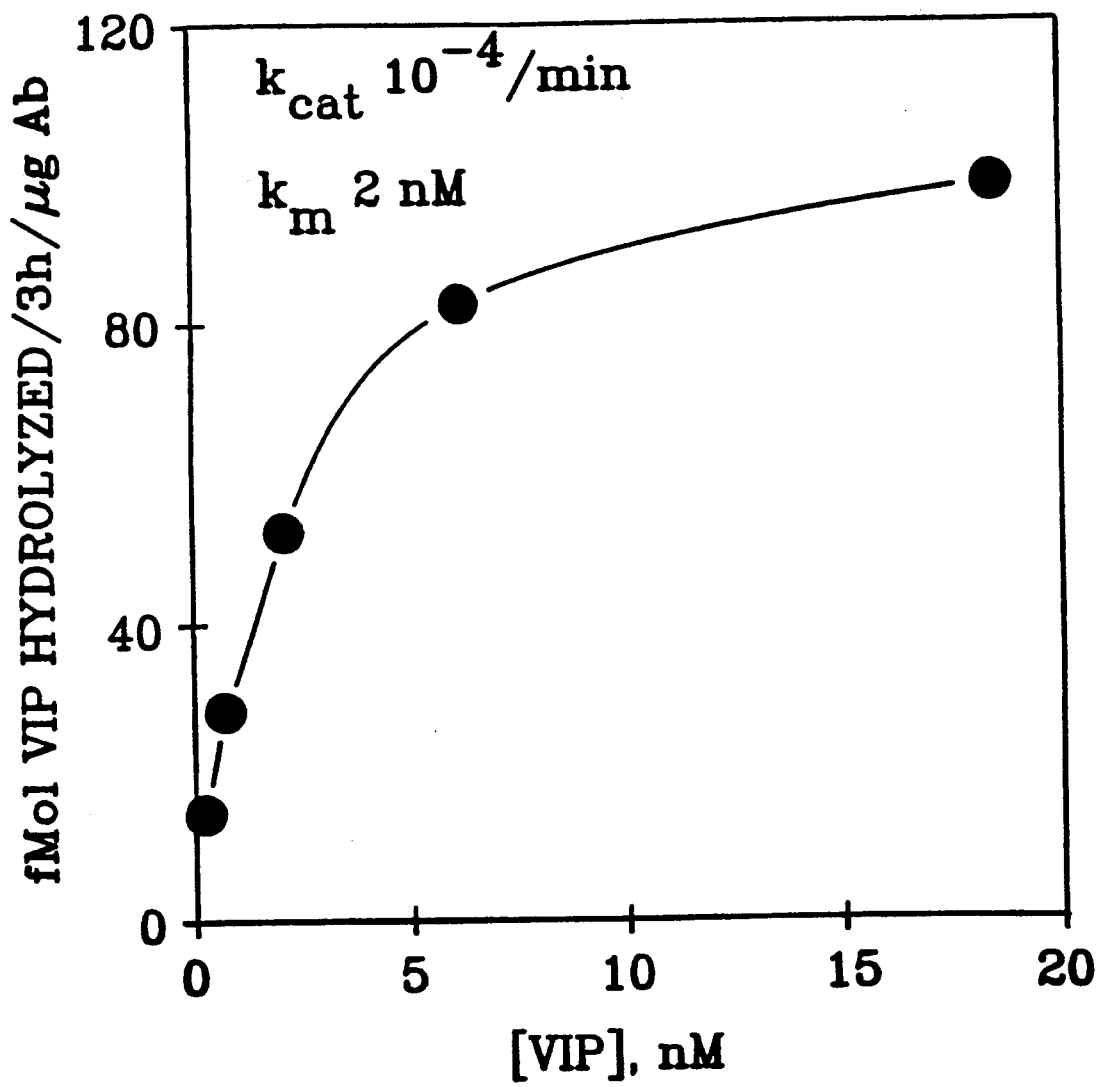
FIG. 3 shows the saturability of VIP hydrolysis by c23.5 IgG fitted to the Michaelis-Menten equation.

Evaluation using TCA precipitation to separate intact VIP from fragments indicates that hydrolysis of VIP by antibody c23.5 follows Michaelis-Menten kinetics ($K_m$ 2 nM, kcat $8 \times 10^{-5}$/min) (FIG. 3). Binding studies under conditions that did not permit VIP hydrolysis (high ionic strength) yielded a $K_d$ estimate of 3.4 nM (37).

The specificity of the observed antibody hydrolytic activity was confirmed by the failure of the antibody to hydrolyze unrelated tripeptide methylcoumarinamides (Boc-L-R-R-MCA; and, Z-R-R-MCA), assayed as the fluorescence of the leaving group [methylcoumarinamide (MCA)] (Excitation wavelength, 370 mm; Emission wavelength, 460 nm). In this experiment, 100 nM c23.5 antibody was incubated with 10 µg/ml substrate in microtiter plated (reaction volume 50 µl) for 14 h in 100 nM Tris-HCl, 50 mM glycine, 0,025% Tween-20 pH 8 (Buffer A). Fluorescence values with the antibody were always <1 unit. In comparison, bovine pancreatic trypsin yielded values of 263, 194 and 179 units using Boc-L-R-R-MCA, P-F-R-MCA and Z-R-R-MCA, respectively.

EXAMPLE 2

Figure 4:
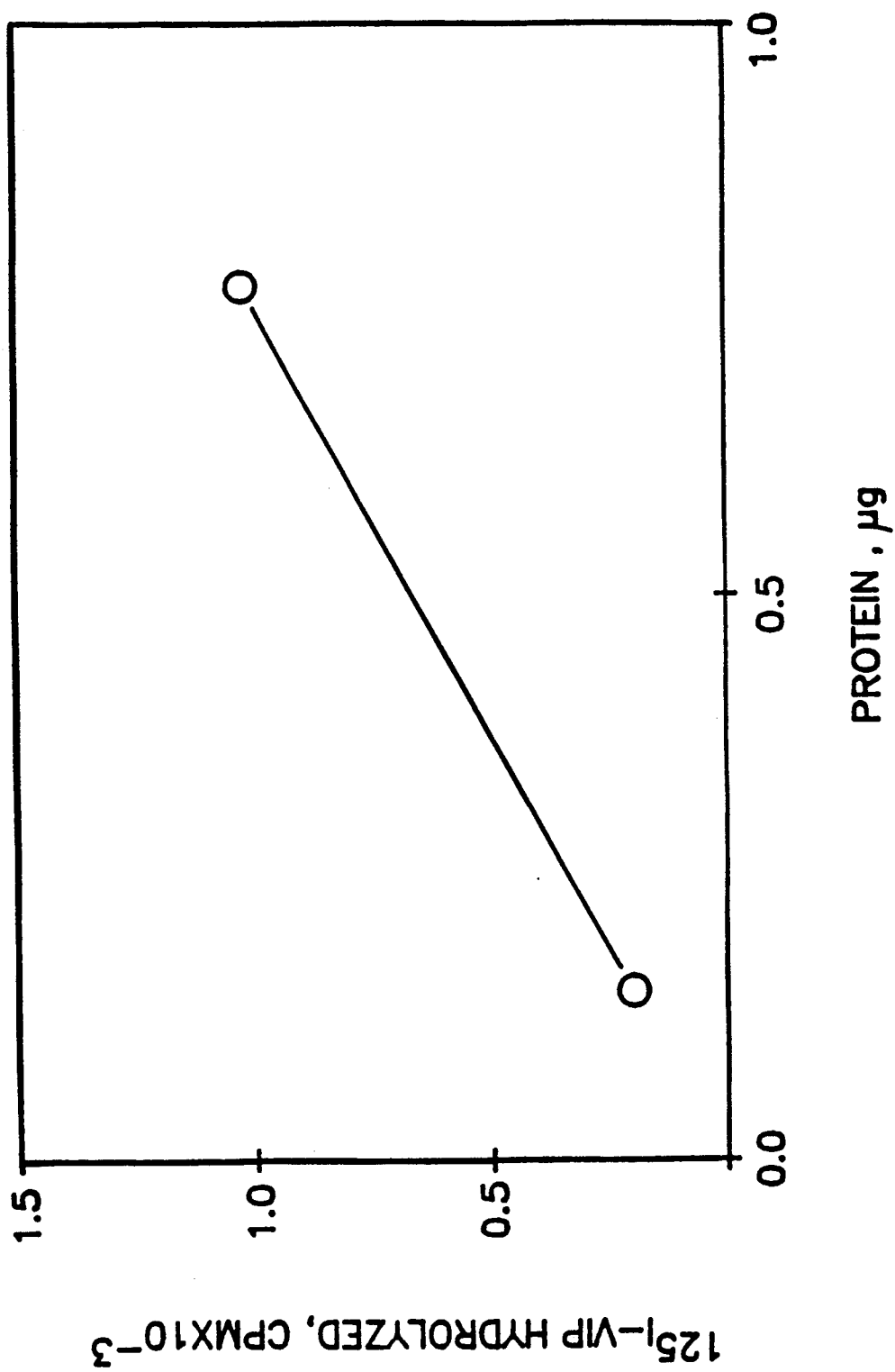
FIG. 4 shows the hydrolysis of $(Tyr^{20}-^{125}I)VIP$ by increasing concentrations of c23.5 light chains purified by gel filtration in quanidinium chloride.

Monoclonal L-Chain Mediated VIP Hydrolysis c23.4 antibody purified by protein G-Sepharose chromatography (Ex. 1) (0.76 mg) was reduced with 2-mercaptoethanol 0.2M for 3 h and then alkylated with iodoacetamide (0.3M) for 15 min, while the pH was maintained at 8 by addition of 1M Tris base. The reduced and alkylated antibody was then treated with 6M guanidinium chloride for 2 h, followed by fractionation by gel filtration in 6M guanidinium chloride on two Superose-12 columns attached in tandem at a flow rate of 0.4 ml/min (Pharmacia, Piscataway, N.J.). The column fractions were dialyzed extensively against Buffer A (see Example 1 for composition) and then fractionated by filtration (Superdex). This purification protocol permitted preparation of a 25 kD L-chain fraction (retention time 60 min) apparently free of H-chain contamination, judged by SDS-polyacrylamide gel electrophoresis. Earlier eluting fractions from the column appeared to be enriched in H-chains, but also contained significant amounts of L-chains (26 Kd) and 90 kD constituents which may be H-L dimers. The pure L-chain fraction exhibited VIP binding ($9 \times 10^3$ CPM/$\mu$g protein) and hydrolysis (FIG. 4) when assayed according to Paul etal. (19).

Figure 5:
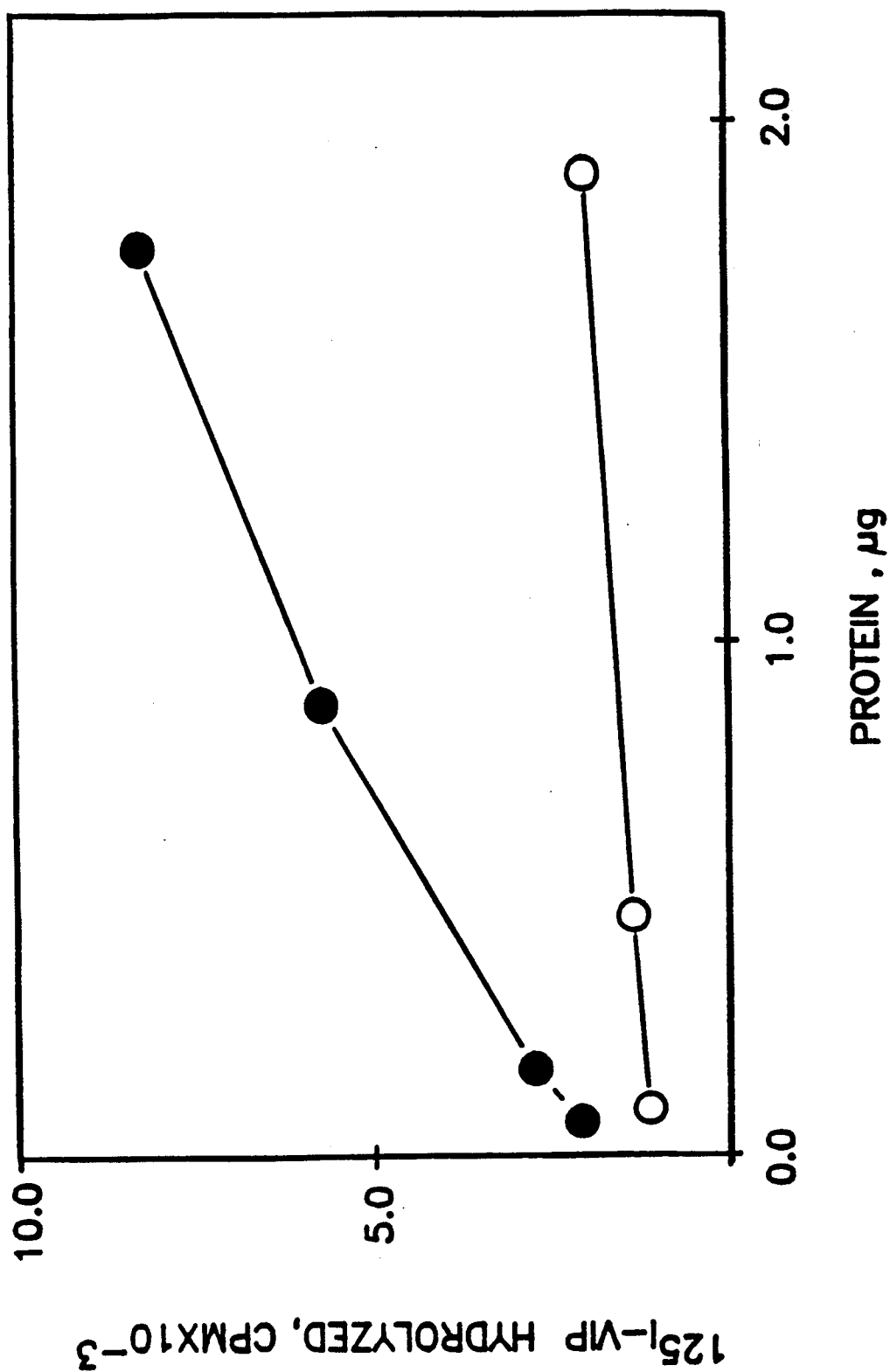
FIG. 5 shows the hydrolysis of $(Tyr^{20}-^{125}I)VIP$ by increasing concentrations of c23.5 light chains (solid circles) recovered by electroelution following SDS-polycrylamide gel electrophoresis of IgG under reducing conditions and intact IgG (open circles) recovered by similar means following electrophoresis of the IgG under non-reducing conditions.

In a second experiment, c23.5 antibody was treated with 143 mM 2-mercaptoethanol, and 0.4% SDS in a Tris-HCL buffer, pH 6.8 and electrophoresed on a 7.5% SDS-polyacrylamide gel using a Schleicher and Schuellminielectrophoresis system (22-30 mA/gel). The bands corresponding to the H-chain (60 kD) and L-chain (25 kD) were excised, electroeluted (Biorad Model 422 eluter; 8-10 mA/elution tube), the eluate was electrodialyzed against buffer that did not contain SDS and subjected to Extractigel chromatography (Pierce, Rockford, Ill.) in 50 mM Tris-HCl, pH 9, to remove residual SDS. The samples were then brought into Buffer A by 2-cycles of ultrafiltration on Centriprep-10 ultrafilters (Amicon). The L-chain preparation displayed dose-dependent. hydrolysis (FIG. 5).

EXAMPLE 3

Cloning and Sequencing of c23.5 L-Chain and H-Chain cDNA

Total RNA was prepared from $10^8$ cells (c23.5) by the one-step guanidine-isothiocyanate method. cDNA was made from the c23.5 RNA using reverse transcriptase. Forward primers used for the reverse transcriptase reaction and forward and back primers used to amplify the cDNA for $V_L$, L-chain ($V_L+C_L$), $V_H$ and Fd-chain ($V_H+C_HL$) are shown in Table 1. The primers were designed based on consensus sequences present in L-chain (kappa) and heavy chains ($IgG_{2a}$) (38-42). BamHI or XbaI restriction sites were incorporated into the backward primers and EcoRl sites into the forward primers to facilitate cloning. The cDNA was then amplified by polymerase chain reaction using Taq DNA polymerase (30 cycles; 1 min at 95° C., 2 min at 55° C. and 3 min at 72° C. for each cycle). The amplified cDNA exhibited the expected sizes determined by agarose gel electrophoresis. The L-chain variable region cDNA was then cloned into a pBluescriptIIKS+ vector (Stratagene, La Jolla, Calif.) via the EcoRI and XbaI restriction sites. The ligated vector was introduced into Escherichia coli and transformed colonies (white) were selected in LB agar supplemented with X-gal and ampicillin. Plasmid DNA prepared from these colonies and digested with EcoRI exhibited a larger size (3.35 kb) than the pBluescript (3.0 kb), corresponding to the length of the DNA insert. The DNA insert was sequenced by the dideoxy chain Germination method using $^{35}$S-ATP precursor and T3 and T7 sequencing primers. Ten colonies containing inserts were sequenced and the deduced sequence (Table 2) in each case was identical. The H-chain variable region cDNA was cloned and sequenced in a similar manner.

TABLE 1

PCR PRIMERS FOR pBluescript II

L-Chain Primers (SEQ ID NO:1)

| | | EcoRI | |
|---|---|---|---|
| L-v 5' | 5' | GGAATTC GAC ATT GTG CTG ACC CAR TCT CC | 3' |

(SEQ ID NO:2)

| | | BamHI | |
|---|---|---|---|
| L-v 3' | 5' | cgggatcc cag ctt ggt ccc ccc icc gaa cg | 3' |

(SEQ ID NO:3)

| | | XbaI | |
|---|---|---|---|
| L-c 3' | 5' | gctctaga ctc att cct gtt gaa gct ctt gac | 3' |

H-Chain Primers (SEQ ID NO:4)

| | | EcoRI | |
|---|---|---|---|
| H-v 5' | 5' | GGAATTC GAG GTI CAG CTT CAG SAG TCW GG | 3' |

(SEQ ID NO:5)

| | | BamHI | |
|---|---|---|---|
| H-v 3' | 5' | cgggatcc ggt gas crk ggt icc tkk gcc cca g | 3' |

(SEQ ID NO:6)

| | | XbaI | |
|---|---|---|---|
| H-c 3' | 5' | gctctaga tgt trt ggg cac tct ggg ctc | 3' |

Synthetic oligonucleotide primers used to amplify c23.5 L-chains (SEQ ID NO:1 and SEQ ID NO:3), $V_L$(SEQ ID NO:1 and SEQ ID NO:2), Fd (SEQ ID NO:4 and SEQ ID NO:6), and $V_H$ (SEQ ID NO:4 and SEQ ID NO:5). Forward primers (5') are shown in upper case and backward primers (3') in lower case. R is G or A; K is G or T; S is G or C; W is A or T and I is inosine.

TABLE 2

Sequence of c-23:5 VL (SEQ ID NOS: 7 and 8)

```
1                                  21                                  41
GAC ATT GTG CTG ACC CAG TCT CCT GCC TCC CAG TCT GCA TCT CTG
asp ile val leu thr gln ser pro ala ser gln ser ala ser leu 61                                  81
GGA GAA AGT GTC ACC ATC ACA TGC CTG GCA AGT CAG ACC ATT GGT
gly glu ser val thr ile thr cys leu ala ser gln thr ile gly
```

TABLE 2-continued

```
         101                              121
ACA TGG TTA CCA TGG TAT CAG CAG AAA CTA GGG AAA TCT CCT CAG
thr trp leu pro trp tyr gln gln lys leu gly lys ser pro gln 141                              161
CTC CTG ATA TAT GCT GCA ACC AGC TTG GCA GAT GGG GTC CCA TCA
leu leu ile tyr ala ala thr ser leu ala asp gly val pro ser 181                      201                          221
AGG TTC AGT GGT AGT GGA TCT GCC ACA AAA TTT TCT TTC AAG ATC
arg phe ser gly ser gly ser ala thr lys phe ser phe lys ile 241                              261
AGC AGC CTA CAG GCT GAA GAT TTT GTA AGT TAT AAC TGT CAA CAT
ser ser leu gln ala glu asp phe val ser tyr asn cys gln his 281                          301
CTT TAC AGT ACT CCG CTC ACG TTC GGC GGG GGG ACC AAG CTG
leu tyr ser thr pro leu thr phe gly gly gly thr lys leu
```

Sequence of c-23:5 VH (SEQ ID NOS: 9 and 10)

```
1                        21                           41
GAG GTG CAG CTT CAG GAG TCT GGG GGA GGC TTA GTG AAG CCT GGA
glu val gln leu gln glu ser gly gly gly leu val lys pro gly 61                           81
GGG TCC CTG AAA CTC TCC TGT GCA GCC TCT GGA TTC ACT TTC AGT
gly ser leu lys leu ser cys ala ala ser gly phe thr phe ser 101                          121
ATC TAT GGC ATG TCT TGG TTT CGC CAG ACT CCG GAG AAG AGG CTG
ile tyr gly met ser trp phe arg gln thr pro glu lys arg leu 141                              161
GAG TGG GTC GCA ACA ATT AGT GGT GGT GAT ACT TAC ACC TAC TAT
glu trp val ala thr ile ser gly gly asp thr tyr thr tyr tyr 181                      201                          221
CCA GAC AGT GTG AAG GGG CGA TTC ACC ATC TCC AGA GAC AAT GCC
pro asp ser val lys gly arg phe thr ile ser arg asp asn ala 241                              261
AAG AAC AAC CTG TTC CTG CAA ATG AGC AGT CTG AGG TCT GAG GAC
lys asn asn leu phe leu gln met ser ser leu arg ser glu asp 281                          301
ACG GCC TTG TAT TTC TGT GGA AGA GGG ATT GCT TAC TGG GGC CAA
thr ala leu tyr phe cys gly arg gly ile ala tyr trp gly gln 321
GGG ACT CTG GTC ACT GTC TCT GCA
gly thr leu val thr val ser ala
```

Underlining indicates complementarity determining regions (CDR's) of the antibody chain.

EXAMPLE 4

Evidence for Subunit Rearrangement

Antibodies are composed of four subunits held by disulfide bonds. Reduction and reformation of disulfide bonds could conceivably result in formation of a variety of antibody oligomers (e.g., H-H, L-L, H-L). Analogous disulfide bond exchange reactions are shown to occur in other oligomeric proteins (32). The importance of such rearrangements for antibody binding activity is probably minimal since dissociated antibody subunits display low binding activity, and variant molecules composed of incorrectly paired subunits are also likely to possess low binding activity. In regard to antibody catalysis, however, it has been observed that purified L-chains hydrolyze VIP faster than undissociated antibody preparations. Formation of rearranged antibody oligomers may well be accompanied by increased hydrolytic activity, if homologous H-chains are better inhibitors of L-chain catalytic activity than heterologous H-chains. Evidence that subunit rearrangement in VIP antibodies may form new catalytic species is as follows.

Figure 8:
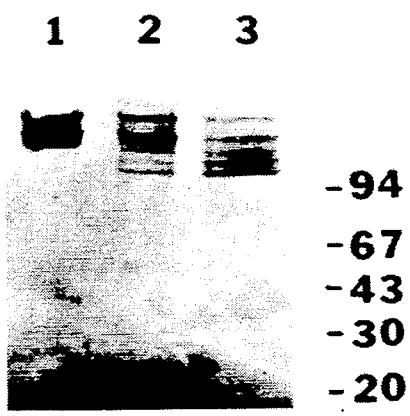
FIG. 8 shows the silver stained SDS-polyacrylamide gel showing the results of non-reducing electrophoresis of fractions corresponding to retention times 32–33 (lane 1), 34 (lane 2) and 35–38 (lane 3) in FIG. 7.
Figure 6:
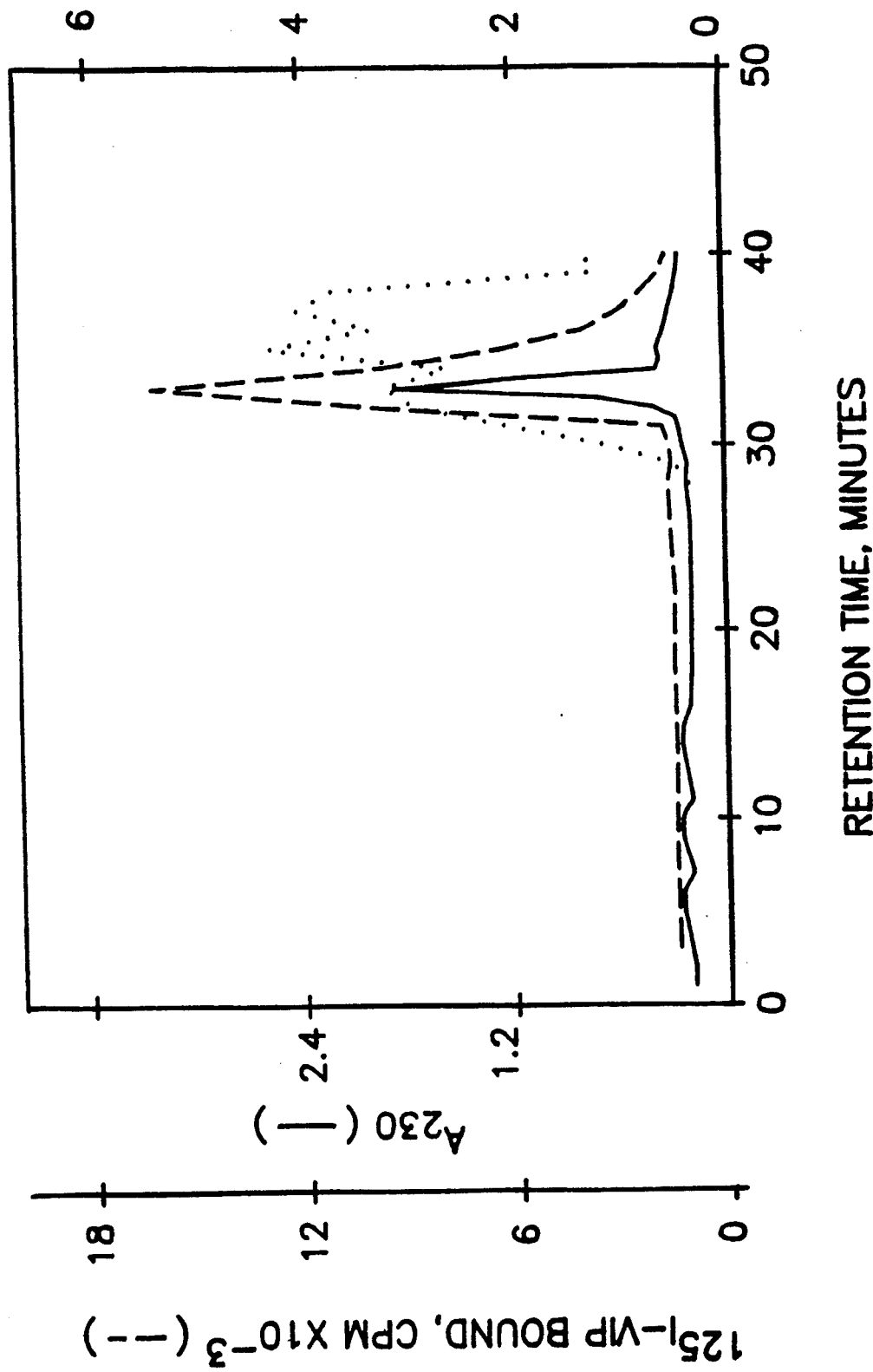
FIG. 6 shows the anion exchange fractionation (Mono Q column) of c23.5 IgG previously purified by chromatography on immobilized protein G.
Figure 7:
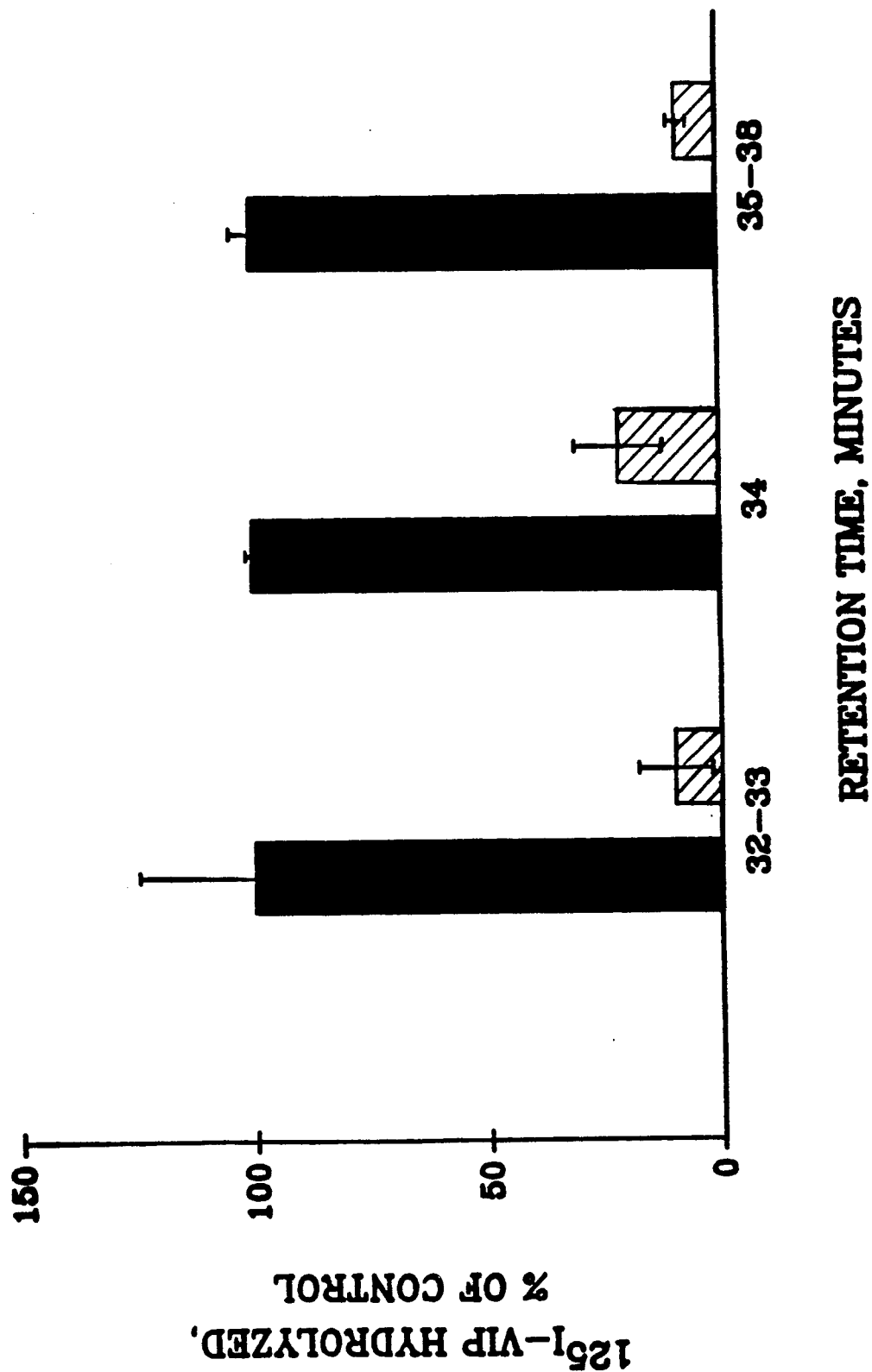
FIG. 7 shows the loss of $(Tyr^{20}-^{125}I)VIP$ hydrolytic activity present in fractions obtained from the anion exchange column of FIG. 6 by adsorption with immobilized anti-mouse IgG (hatched columns) wherein control adsorptions were done with equivalent amounts of immobilized anti-rabbit IgG and the results represent fractions corresponding to retention times 32–33, 34, and 35–38 minutes.

Anion exchange chromatography (Mono Q column, Pharmacia) (0–1M NaCl in 40 min; 1 min fractions were collected) of 0.55 mg c23.5 antibody that had previously been purified by affinity chromatography on immobilized Protein G produced a sharply eluting protein peak, corresponding to fractions 32 and 33 (FIG. 6). Following dialysis to remove NaCl, the effluent fractions were assayed for VIP hydrolysis. Fractions corresponding to the main protein peak (fractions 32–33) displayed VIP hydrolytic activity. In addition, VIP hydrolytic activity was observed in fractions 34–38, located at the trailing edge of the protein peak was evident. To determine whether the hydrolytic activity was due to antibodies, the fractions (0.03 ml) were treated with 0.22 ml gel of anti-mouse IgG conjugated to Sepharose (Organon Teknika, Durham, N.C.) or an equivalent amount of control anti-rabbit IgG conjugated to Sepharose (Jackson Immuno Research, West Grove, Pa.) for 13 h in a final volume of 5 ml Buffer A (see Ex. 1), and the supernatants (0.05 ml) of the gels were assayed for VIP hydrolysis. The hydrolytic activity in all fractions was nearly completely adsorbed by immobilized anti-mouse IgG, but not by immobilized anti-rabbit IgG (FIG. 7). SDS-polyacrylamide gel electrophoresis under reducing conditions and immunoblotting using a specific anti-mouse IgG antibody showed that all fractions were composed of 60 kD H- and 25 kD L-chains. The late eluting fractions also contained a 90 kD band that was stainable with the anti-mouse IgG and represents an H-L dimer. Electrophoresis under non-reducing conditions revealed that the main protein peak was composed of intact 150 kD antibodies while the trailing peak was composed of 90–120 kD bands, representing antibody oligomers (FIG. 8).

EXAMPLE 5

Characterization of Anti-VIP Antibody

A. Kinetic Data and Binding Effects

Figure 9:
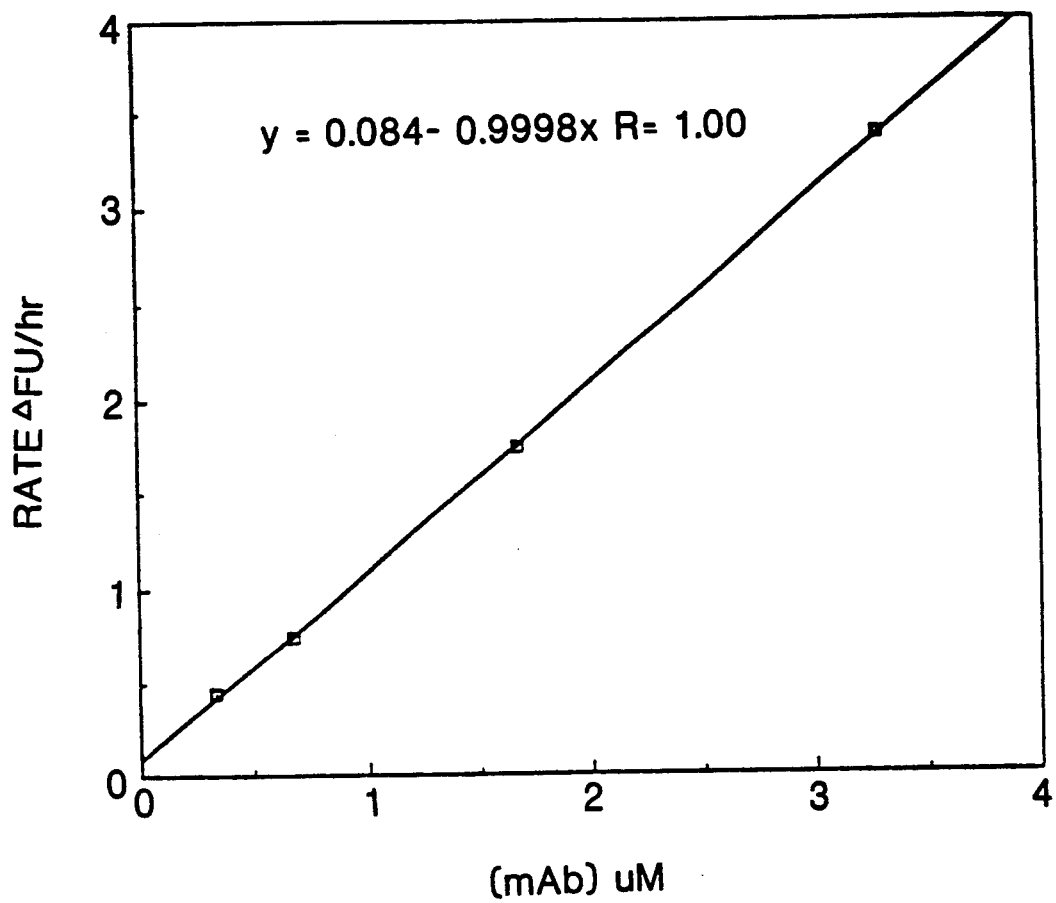
FIG. 9 shows the hydrolysis of $(Abz)RKQMAVK-KY(NO_2)D$ by increasing concentrations of c23.5 IgG estimated as the increase in fluorescence of the reaction mixtures.

VIP has been previously observed to undergo cleavage by human autoantibodies at several bonds located between residues 14 and 22 (36). A synthetic peptide mimic [ABz-RKQMAVKKY(NO2)D] of VIP(14-22) (RKQMAVKKY (SEQ ID No. 12); designated pep2) was tested as substrate for the monoclonal antibody. The anthraniloyl group at the N-terminus of this synthetic peptide in combination with the Y(NO$_2$) residue close to the C-terminus functions as an intramolecularly quenched fluorescence reporter system for hydrolysis at peptide bonds located between the fluorophore (ABz) and quencher [Y(NO2)]. Synthesis of this peptide was according to Meldal, M. et al. (43). Treatment of pep2 with the increasing concentrations of c23.5 antibody monoclonal VIP antibody resulted in progressive hydrolysis, determined by an increase in fluorescence emission at 420 nm (excitation wavelength, 370 nm) (FIG. 9).

Figure 10:
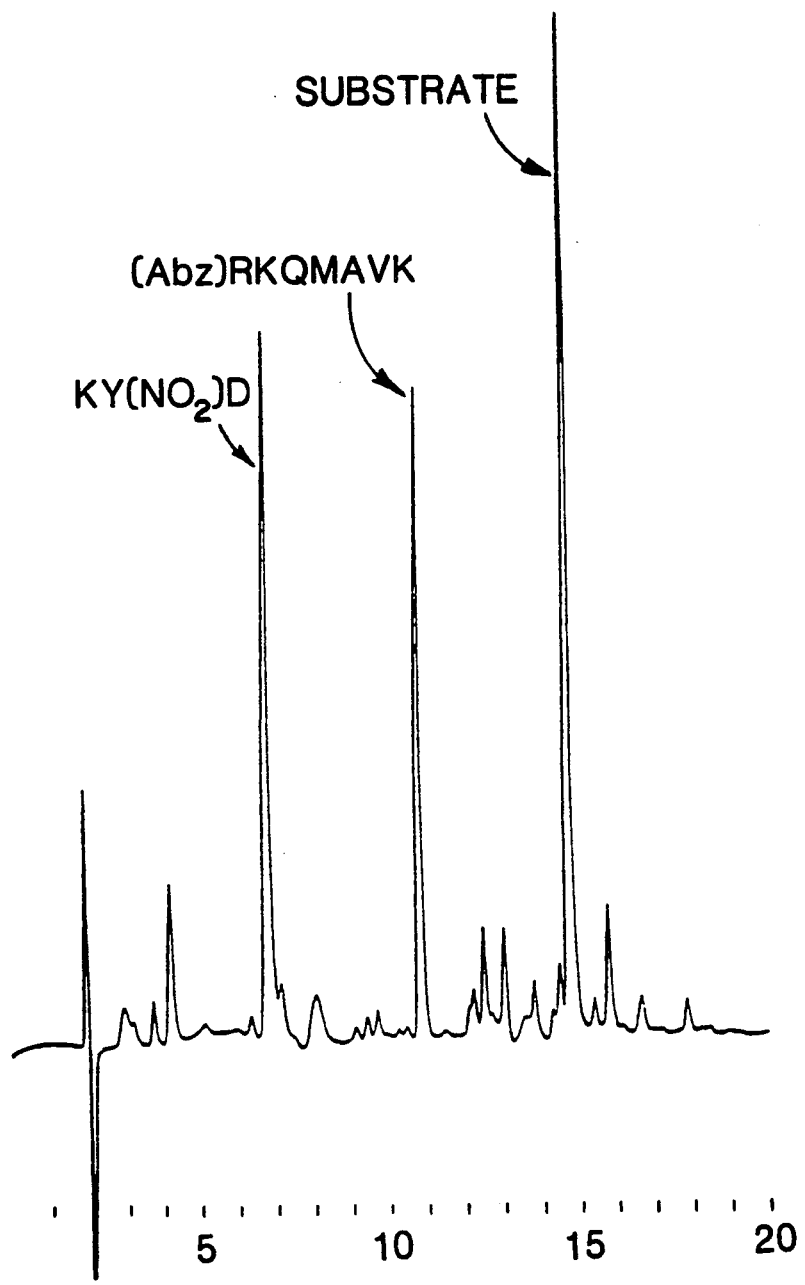
FIG. 10 shows the reverse phase HPLC of $(Abz)RK-QMAVKKY(NO_2)D$ treated with c23.5 IgG wherein identification of the peptide peaks was by amino acid sequencing.

Initial rate data obtained by varying the substrate concentrations were consistent with Michaelis-Menten kinetics. Reversed-phase HPLC analysis on a C-18 column using trifluoroacetic acid in acetonitrile for elution, showed the appearance of two new peptide peaks following treatment of pep1 (20 μM) with c23.5 antibody (20 μM) for 100 h in MOPS buffer (FIG. 10). These were sequenced on an automated Applied Biosystems peptide liquide phase sequenator equipped with online PTH-amino acid detection. The two peptides were identified to be RKQMAVK (SEQ ID NO: 13) and KY(NO2)D, indicating that the scissile bond is a K—K bond, corresponding to $K^{20}$-$K^{21}$ in intact VIP.

REFERENCES

1. Pauling, L. *Nature* 161:707 (1948)
2. Kohen, F. Kim, J. B., Linder, H. R., Eshkar, Z., Green, A.B. Antibody enhanced hydrolysis of steroid esters, *Biochemica et Biophysica Acta* 629, 328–337 (1980).
3. Pollack, S. J., Jacobs, J. W., Schultz, P. J., *Science* 234, 1570 (1986).
4. Tramontano, A., Amman, A. A., Lerner, R. A., *J. Am. Chem et Soc.* 110, 2282 (1988).
5. Janda, K. D., Schloeder, D., Benkovic, S. J., Lerner, R. A., *Science* 241, 1188 (1988)
6. Durfor, C. N., Bolin, R. J., Sugasawara, R. J., Massey, R. J., Jacobs, J. W., Schultz, P. J., *J. Am. Chem, Soc.* 110, 8713 (1988).
7. Jackson, D. Y., Jacobs, J. W., Sugasawara, R., Reich, S. H., Bartlett, P. A., Schultz, P. G., *J. Am. Chem. Soc.* 110, 4841 (1988).
8. Hilvert, D., Carpenter, S. H., Nared, K. D., Auditor, N. T., *Proc. Natl. Acad. Sci. USA* 85, 4953 (1988).
9. Shokat, K. Leumann, C. H., Sugasawara, R., Schultz, P.G., *Angew. Chem. Int. Ed. Engl.* 27, 1172 (1988).
10. Titmas et al., R. C., Peptide Analogs and Their Use As Hapten to Elect Antibodies PCT US89/01951 filed May 14, 1989.
11. Suckling, C. J., Tedford, C. M., Proctor, G. R., Khalaf, A. I., Bence, L. M. and Stimson, W. H. 1991 *CATALYTIC ANTIBODIES*, Wiley, Chichester (Ciba Foundation Symposium 159) p. 201–210.
12. Iverson, B. L. and Lerner, R. A., *Science* 243, 1184 (1989).
13. Roholt, O., Onoue, K., and Pressman, D. *Biochemistry* 51, 173, (164).
14. Ward, E. S., Gussow, D. Griffiths, A. D., Jones, P. T. and Winter, G. *Nature*, 341, 544–546 (1989).
15. Edelman, G. M., Olins, D. E., Gally, J. A. and Zinder, N. D. *Proc. Natl. Acad. Sci.*, 50, 753–761 (1963).
16. Franek, F. and Nezlin, R. S. *Folia Microbiol.*, 8, 128–130 (1963).
17. Franek, F. and Nezlin, R. S. *Biokhimiya*, 28, 193 (1963).
18. Massey, R. J. et al. U.S. Pat. No. 4,888,281.
19. Paul, S., Volle, D. J., Beach, C. M., Johnson, D. R., Powell, M. J. and Massey, R. J.: Catalytic hydrolysis of vasoactive intestinal peptide by human autoantibody. *Science*, 244, 1158–1162 (1989).
20. Paul, S., Mei, S., Mody, B., Eklund, S. H., Beach, C. M., Massey, R. J. and Hamel, F. Cleavage of VIP at multiple sites by autoantibodies. *J.Biol.Chem*. In press (1991).
21. Mei, S., Mody, B., Eklund, S. H. and Paul, S.: VIP hydrolysis by antibody light chains. *J.Biol.Chem*. In press (1991).
22. Paul, S., Volle, D. J. and Mei, S.: Affinity chromatography of catalytic autoantibody to vasoactive intestinal peptide. *J.Immunol.*, 145, 1196–1199 (1990).
23. Paul, S., Volle, D. J., Powell, M. J. and Massey, R. J.: Site specificity of a catalytic vasoactive intestinal peptide antibody: An inhibitory VIP subsequence distant from the scissile peptide bond. *J.Biol.Chem.*, 365, 11910–11913 (1990).
24. Paul, S.: A new effector mechanism for antibodies: Catalytic cleavage of peptide bonds. *Cold Spring Harb. Symp. Quant. Biol.*, 54, 283–286 (1989).
25. Paul, S., Johnson, D. J. and Massey, R. J. Binding epitopes and multiple hydrolytic sites recognized by catalytic antibodies. In CIBA Foundation Symp. 159 on Catalytic Antibodies, In Press, (1991). 26. Mutt, V. Vasoactive Intestinal Peptide and related peptides: Isolation and chemistry. *Annals of the New York Academy of Sciences* 527, 1–19 (1988).
27. Paul, S., Mei, S., Mody, B., Eklund, S. H., Beach, C. M., Massey, R. J. and Hamel, F. Cleavage of VIP at multiple sites by autoantibodies. *J.Biol.Chem*. In press 1991 (August issue).
28. Nishi, N., Tsutusumi, A., Morishige, M., Kiyama, S., Fuji, N., Takeyama, M. Yajima, H. Apparent autolysis of the N-terminal tetrapeptide of VIP: *Chem. Pharm. Bull.* 31, 1067–1072 (1983).
29. Davies, D. R., Padlan, E. A. and Sheriff, S.: Antibody-antigen complexes. *Ann. Rev. Biochem.,* 59, 439–474 (1990).
30. French, D. L., R. Laskow, and M. D. Scharff. The role of somatic hypermutation in the generation of antibody diversity. *Science* 244, 1152 (1989).
31. Barrett, A. J.: An introduction to proteinases. In: *Proteinase Inhibitors,* Eds.: A. J. Barrett and G. Salvesen, Elsevier, pp. 3–22 (1986).
32. Creighton, T. E. Disulfide bonds between cystein residues. In Protein Structure: A Practical Approach (Ed. T. E. Creighton) IRL Press, Oxford, U.K., pp. 155–167.
33. Jue et al., Biochemistry 17, 5399–5406, (1978).
34. Paul, S., Said, S. I., Thompson, A. Volle, DJ Agrawol, D. K., Foda, H, and De la Rocha, S. Characterization of autoantibodies to VIP in asthma. *J. Neuroimmunol.,* 23, 133–142 (1989).
35. Brown, G. and Ling, N. R. Murine Monoclonal Antibodies. In Antibodies: A Practical Approach (Ed: D.Cathy) IRL Press, Oxford, U.K. Vol. 1, page 81–104 (1988).
36. Paul et al. *J. of Biol. Chem.* 266, 16128–16134 (1991).
37. Baldwin E. and Schuyltz, P. G., *Generation of a catalytic antibody by site-directed mutagenesis. Science,* 245, 1104–1107 (1989).
38. Kabat, E. A., Wu, T. T., Reid-Miller, M., Perry, H. M. and Gottesman, K. S.: Sequences of proteins of immunological interest (4th ed.), U.S. Department of Health and Human Services.
39. Orlandi, R., Gussow, D. H. Jones, P. Y. and Winter, G.: Cloning immunoglobulin variable domains for expression by the polymerase chain reaction. *Proc. Natl. Acad. Sci. USA,* 86, 3833–3837, (1989).
40. Sastry, L., Alting-Mees, M., Huse, W. D., Short, J. M., Sorge, J. A., Hay, B. N., Janda, K. D. Benkovic, S. J. and Lerner, R. A.: Cloning of the immunological repertoire in *Escherichia coli* for generation of monoclonal catalytic antibodies: Construction of a heavy chain variable region-specific cDNA library. *Proc. Natl. Acad. Sci., USA,* 86, 5728–5732, (1989).
41. Huse, W. D., Sastry, L., Iverson, S. A., Kang, A. S., Alting-Mees, M., Burton, D. R., Benkovic, S. J. and Lerner, R. A.: Generation of a large combinatorial library of the immunoglobulin repertoire in phage lambda. *Science,* 246, 1275–1281, (1989).
42. Larrick, J. W., Danielsson, L., Brenner, C. A., Abrahamson, M., Fry, K. E. and Borrebaeck, C. A. K.: Rapid cloning of rearranged immunoglobulin genes from human hybridoma cells using mixed primers and the polymerase chain reaction. *Biochem. Biophys. Res. Commun.,* 160, 1250–1256, (1989).
43. Meldal, M. et al., Breddam, K., *Analytical Biochemistry,* 195, 141–147, (1991).

What I claim is:

1. A method of catalyzing a chemical reaction of a polypeptide comprising contacting said polypeptide with at least one catalytic monoclonal antibody produced by a process comprising the steps of:
   a. generating a plurality of monoclonal antibodies to an antigen selected from the group consisting of: said polypeptide, and
      a fragment of said polypeptide; and
   b. screening said plurality of monoclonal antibodies to identify a monoclonal antibody which catalyzes said chemical reaction; wherein said polypeptide is vasoactive intestinal peptide and said chemical reaction is hydrolysis of said polypeptide at at least one peptide bond.

2. A method of catalyzing a chemical reaction of a polypeptide comprising contacting said polypeptide with at least one catalytic monoclonal antibody produced by a process comprising the steps of:
   a. immunizing an animal with an antigen selected from the group consisting of
      said polypeptide, and
      a fragment of said polypeptide; and thereby generating antibody-producing lymphocytes from said animal;
   b. removing said antibody-producing lymphocytes from said animal;
   c. fusing said antibody-producing lymphocytes with myeloma cells and thereby producing a plurality of hybridoma cells each producing monoclonal antibodies; and
   d. screening said plurality of monoclonal antibodies to identify a monoclonal antibody which catalyzes the reaction; wherein said polypeptide is vasoactive intestinal peptide and said chemical reaction is hydrolysis of said polypeptide at at least one peptide bond.

3. A process for making a catalytic antibody able to catalyze a chemical reaction of a polypeptide comprising the steps of:
   a. eliciting an immune response to said polypeptide; and
   b. screening immune cells or antibodies resulting from said immune response to identify immune cells or antibodies having the property of catalyzing the chemical reaction of said polypeptide; wherein said polypeptide is vasoactive intestinal peptide and said chemical reaction is hydrolysis of said polypeptide at at least one peptide bond.

4. A process for making a catalytic antibody able to catalyze a chemical reaction of a polypeptide comprising the steps of:
   a. generating a plurality of monoclonal antibodies to an antigen selected from the group consisting of: said polypeptide, and
      a fragment of said polypeptide; and
   b. screening said plurality of monoclonal antibodies to identify a monoclonal antibody having the property of catalyzing the chemical reaction of said polypeptide; wherein said polypeptide is vasoactive intestinal peptide and said chemical reaction is hydrolysis of said polypeptide at at least one peptide bond.

5. A catalytic antibody able to catalyze a chemical reaction of a polypeptide produced by a process comprising the steps of:
   a. eliciting an immune response to the polypeptide; and
   b. screening immune cells or antibodies resulting from said immune response to identify immune cells or antibodies having the property of catalyzing the chemical reaction of said polypeptide; wherein said polypeptide is vasoactive intestinal peptide and said chemical reaction is hydrolysis of said polypeptide at at least one peptide bond.

6. A catalytic antibody able to catalyze a chemical reaction of a polypeptide produced by a process comprising the steps of:
   a. generating a plurality of monoclonal antibodies to an antigen selected from the group consisting of:
      said polypeptide, and
      a fragment of said polypeptide; and
   b. screening said plurality of monoclonal antibodies to identify a monoclonal antibody having the property of catalyzing the chemical reaction; wherein said polypeptide is vasoactive intestinal peptide and said chemical reaction is hydrolysis of said polypeptide at at least one peptide bond.

7. A method of catalyzing a chemical reaction of a reactant comprising contacting said reactant with a catalytic antibody light chain produced by a process comprising the steps of:
   a. generating a plurality of monoclonal antibodies to an antigen selected from the group consisting of:
      i. said reactant,
      ii. a derivative of said reactant, and
      iii. a fragment of said reactant;
   b. screening said plurality of monoclonal antibodies to identify a monoclonal antibody which catalyzes said chemical reaction;
   c. separating said catalytic monoclonal antibody into light chain and other components; and
   d. isolating said light chain component.

8. A method as recited in claim 7 wherein step c comprises the further steps of cleaving said catalytic monoclonal antibody to form an Fab fragment and reducing and then alkylating said Fab fragment under denaturing conditions, and wherein step d comprises fractionation by filtration.

9. A method of catalyzing a chemical reaction of a reactant comprising contacting said reactant with a catalytic antibody light chain produced by a process comprising the steps of:
   a. immunizing an animal with an antigen selected from the group consisting of
      i. said reactant,
      ii. a derivative of said reactant, and
      iii. a fragment of said reactant; and thereby generating antibody-producing lymphocytes in said animal;
   b. removing said antibody-producing lymphocytes from said animal;
   c. fusing said antibody-producing lymphocytes with myeloma cells and thereby producing a plurality of hybridoma cells each producing monoclonal antibodies;
   d. screening said plurality of monoclonal antibodies to identify a monoclonal antibody which catalyzes the reaction; and
   e. obtaining a catalytic antibody light chain of said catalytic monoclonal antibody.

10. The method as recited in claim 9 further comprising producing a catalytic antibody light chain by the steps of:
    a. inserting into a cell at least one nucleic acid sequence coding for a variable region of said catalytic antibody light chain;
    b. replicating said cell; and
    c. expressing said nucleic acid sequence to produce a product having the desired catalytic activity.

11. A process for making a catalytic antibody light chain able to catalyze a chemical reaction of a reactant comprising the steps of:
    a. generating a plurality of monoclonal antibodies to an antigen selected from the group consisting of:
       i. said reactant,
       ii. a derivative of said reactant, and
       iii. a fragment of said reactant;
    b. screening said plurality of monoclonal antibodies to identify a monoclonal antibody which catalyzes said chemical reaction;
    c. separating said catalytic monoclonal antibody into light chain and other components; and
    d. isolating said light chain component.

12. The process as recited in claim 11 wherein step c comprises the further steps of cleaving said catalytic monoclonal antibody to form an Fab fragment and reducing and then alkylating said Fab fragment under denaturing conditions, and wherein step d comprises fractionation by filtration.

13. A process for making a catalytic antibody light chain able to catalyze a chemical reaction of a reactant comprising the steps of:
    a. immunizing an animal with an antigen selected from the group consisting of
       i. said reactant,
       ii. a derivative of said reactant, and
       iii. a fragment of said reactant, thereby generating antibody-producing lymphocytes in said animal;
    b. removing said antibody-producing lymphocytes from said animal;
    c. fusing said antibody-producing lymphocytes with myeloma cells and thereby producing a plurality of hybridoma cells each producing monoclonal antibodies;
    d. screening said plurality of monoclonal antibodies to identify a monoclonal antibody which catalyzes the reaction; and
    e. obtaining a catalytic antibody light chain of said catalytic monoclonal antibody.

14. A catalytic antibody light chain able to catalyze a chemical reaction of a reactant produced by a process comprising the steps of:
    a. generating a plurality of monoclonal antibodies to an antigen selected from the group consisting of:
       i. said reactant,
       ii. a derivative of said reactant, and
       iii. a fragment of said reactant;
    b. screening said plurality of monoclonal antibodies to identify a monoclonal antibody which catalyzes said chemical reaction;
    c. separating said catalytic monoclonal antibody into light chain and other components; and
    d. isolating said light chain component.

15. A catalytic antibody light chain as recited in claim 14 wherein step c comprises the further steps of cleaving said catalytic monoclonal antibody to form an Fab fragment and reducing and then alkylating said Fab fragment under denaturing conditions, and wherein step d comprises fractionation by filtration.

16. A catalytic antibody light chain able to catalyze a chemical reaction of a reactant produced by a process comprising the steps
   a. immunizing an animal with an antigen selected from the group consisting of
      i. said reactant,
      ii. a derivative of said reactant, and
      iii. a fragment of said reactant; and thereby generating antibody-producing lymphocytes in said animal;
   b. removing said antibody-producing lymphocytes from said animal;
   c. fusing said antibody-producing lymphocytes with myeloma cells and thereby producing a plurality of hybridoma cells each producing monoclonal antibodies;
   d. screening said plurality of monoclonal antibodies to identify a monoclonal antibody which catalyzes the reaction; and
   e. obtaining a catalytic antibody light chain of said catalytic monoclonal antibody.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( A ) NAME/KEY: miscfeature
        ( B ) LOCATION: 25
        ( D ) OTHER INFORMATION: /note="Location 25 (R) represents G or A"

( x i ) SEQUENCE DESCRIPTION: SEQ ID NO:1:

GGAATTCGAC ATTGTGCTGA CCCARTCTCC     30

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i x ) FEATURE:
        ( A ) NAME/KEY: modifiedbase
        ( B ) LOCATION: 24
        ( D ) OTHER INFORMATION: /modbase=i ( x i ) SEQUENCE DESCRIPTION: SEQ ID NO:2:

CGGGATCCCA GCTTGGTCCC CCCNCCGAAC G     31

( 2 ) INFORMATION FOR SEQ ID NO:3:

(i) SEQUENCE CHARACTERISTICS:
  (A) LENGTH: 32 base pairs
  (B) TYPE: nucleic acid
  (C) STRANDEDNESS: single
  (D) TOPOLOGY: linear (xi) SEQUENCE DESCRIPTION: SEQ ID NO:3:

GCTCTAGACT CATTCCTGTT GAAGCTCTTG AC    32

(2) INFORMATION FOR SEQ ID NO:4:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ix) FEATURE:
    (A) NAME/KEY: miscfeature
    (B) LOCATION: 13..28
    (D) OTHER INFORMATION: /note="Location 23 (S) represents
        G or C; Location 28 (W) represents A
        or T."

(ix) FEATURE:
    (A) NAME/KEY: modifiedbase
    (B) LOCATION: 13
    (D) OTHER INFORMATION: /modbase=i (xi) SEQUENCE DESCRIPTION: SEQ ID NO:4:

GGAATTCGAG GTNCAGCTTC AGSAGTCWGG    30

(2) INFORMATION FOR SEQ ID NO:5:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ix) FEATURE:
    (A) NAME/KEY: miscfeature
    (B) LOCATION: 14..26
    (D) OTHER INFORMATION: /note="Location 14 (S) represents
        G or C, Location 16 (R) represents G
        or A, Locations 17,25,26 (K)
        represent G or T."

(ix) FEATURE:
    (A) NAME/KEY: modifiedbase
    (B) LOCATION: 21
    (D) OTHER INFORMATION: /modbase=i (xi) SEQUENCE DESCRIPTION: SEQ ID NO:5:

CGGGATCCGG TGASCRKGGT NCCTKKGCCC CAG    33

(2) INFORMATION FOR SEQ ID NO:6:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ix) FEATURE:
    (A) NAME/KEY: miscfeature
    (B) LOCATION: 13
    (D) OTHER INFORMATION: /note="Location 13 (R) represents
        G or A"

(xi) SEQUENCE DESCRIPTION: SEQ ID NO:6:

GCTCTAGATG TTRTGGGCAC TCTGGGCTC    29

(2) INFORMATION FOR SEQ ID NO:7:

(i) SEQUENCE CHARACTERISTICS:
  (A) LENGTH: 312 base pairs
  (B) TYPE: nucleic acid
  (C) STRANDEDNESS: single
  (D) TOPOLOGY: linear (xi) SEQUENCE DESCRIPTION: SEQ ID NO:7:

```
GACATTGTGC TGACCCAGTC TCCTGCCTCC CAGTCTGCAT CTCTGGGAGA AAGTGTCACC      60
ATCACATGCC TGGCAAGTCA GACCATTGGT ACATGGTTAC CATGGTATCA GCAGAAACTA     120
GGGAAATCTC CTCAGCTCCT GATATATGCT GCAACCAGCT TGGCAGATGG GGTCCCATCA     180
AGGTTCAGTG GTAGTGGATC TGCCACAAAA TTTTCTTTCA AGATCAGCAG CCTACAGGCT     240
GAAGATTTTG TAAGTTATAA CTGTCAACAT CTTTACAGTA CTCCGCTCAC GTTCGGCGGG     300
GGGACCAAGC TG                                                         312
```

(2) INFORMATION FOR SEQ ID NO:8:

(i) SEQUENCE CHARACTERISTICS:
    (A) LENGTH: 104 amino acids
    (B) TYPE: amino acid
    (C) STRANDEDNESS: single
    (D) TOPOLOGY: linear (xi) SEQUENCE DESCRIPTION: SEQ ID NO:8:

```
Asp Ile Val Leu Thr Gln Ser Pro Ala Ser Gln Ser Ala Ser Leu Gly
 1               5                  10                  15
Glu Ser Val Thr Ile Thr Cys Leu Ala Ser Gln Thr Ile Gly Thr Trp
                20                  25                  30
Leu Pro Trp Tyr Gln Gln Lys Leu Gly Lys Ser Pro Gln Leu Leu Ile
            35                  40                  45
Tyr Ala Ala Thr Ser Leu Ala Asp Gly Val Pro Ser Arg Phe Ser Gly
        50                  55                  60
Ser Gly Ser Ala Thr Lys Phe Ser Phe Lys Ile Ser Ser Leu Gln Ala
65                  70                  75                  80
Glu Asp Phe Val Ser Tyr Asn Cys Gln His Leu Tyr Ser Thr Pro Leu
                85                  90                  95
Thr Phe Gly Gly Gly Thr Lys Leu
               100
```

(2) INFORMATION FOR SEQ ID NO:9:

(i) SEQUENCE CHARACTERISTICS:
    (A) LENGTH: 339 base pairs
    (B) TYPE: nucleic acid
    (C) STRANDEDNESS: single
    (D) TOPOLOGY: linear (xi) SEQUENCE DESCRIPTION: SEQ ID NO:9:

```
GAGGTGCAGC TTCAGGAGTC TGGGGGAGGC TTAGTGAAGC CTGGAGGGTC CCTGAAACTC      60
TCCTGTGCAG CCTCTGGATT CACTTTCAGT ATCTATGGCA TGTCTTGGTT TCGCCAGACT     120
CCGGAGAAGA GGCTGGAGTG GGTCGCAACA ATTAGTGGTG GTGATACTTA CACCTACTAT     180
CCAGACAGTG TGAAGGGGCG ATTCACCATC TCCAGAGACA ATGCCAAGAA CAACCTGTTC     240
CTGCAAATGA GCAGTCTGAG GTCTGAGGAC ACGGCCTTGT ATTTCTGTGG AAGAGGGATT     300
GCTTACTGGG GCCAAGGGAC TCTGGTCACT GTCTCTGCA                            339
```

(2) INFORMATION FOR SEQ ID NO:10:

(i) SEQUENCE CHARACTERISTICS:
    (A) LENGTH: 113 amino acids
    (B) TYPE: amino acid (C) STRANDEDNESS: single
(D) TOPOLOGY: linear (xi) SEQUENCE DESCRIPTION: SEQ ID NO:10:

| Glu | Val | Gln | Leu | Gln | Glu | Ser | Gly | Gly | Gly | Leu | Val | Lys | Pro | Gly | Gly |
| 1 | | | | 5 | | | | | 10 | | | | | 15 | |
| Ser | Leu | Lys | Leu | Ser | Cys | Ala | Ala | Ser | Gly | Phe | Thr | Phe | Ser | Ile | Tyr |
| | | | 20 | | | | | 25 | | | | | 30 | | |
| Gly | Met | Ser | Trp | Phe | Arg | Gln | Thr | Pro | Glu | Lys | Arg | Leu | Glu | Trp | Val |
| | | 35 | | | | | 40 | | | | | 45 | | | |
| Ala | Thr | Ile | Ser | Gly | Gly | Asp | Thr | Tyr | Thr | Tyr | Tyr | Pro | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Asn | Asn | Leu | Phe |
| 65 | | | | | 70 | | | | | 75 | | | | | 80 |
| Leu | Gln | Met | Ser | Ser | Leu | Arg | Ser | Glu | Asp | Thr | Ala | Leu | Tyr | Phe | Cys |
| | | | | 85 | | | | | 90 | | | | | 95 | |
| Gly | Arg | Gly | Ile | Ala | Tyr | Trp | Gly | Gln | Gly | Thr | Leu | Val | Thr | Val | Ser |
| | | | 100 | | | | | 105 | | | | | 110 | | |
| Ala | | | | | | | | | | | | | | | |

(2) INFORMATION FOR SEQ ID NO:11:

(i) SEQUENCE CHARACTERISTICS:
(A) LENGTH: 28 amino acids
(B) TYPE: amino acid
(C) STRANDEDNESS: single
(D) TOPOLOGY: linear (xi) SEQUENCE DESCRIPTION: SEQ ID NO:11:

| His | Ser | Asp | Ala | Val | Phe | Thr | Asp | Asn | Tyr | Thr | Arg | Leu | Arg | Lys | Gln |
| 1 | | | | 5 | | | | | 10 | | | | | 15 | |
| Met | Ala | Val | Lys | Lys | Trp | Leu | Asn | Ser | Ile | Leu | Asn | | | | |
| | | | 20 | | | | | 25 | | | | | | | |